(12) United States Patent
Pacioretty et al.

(10) Patent No.: US 8,093,292 B2
(45) Date of Patent: *Jan. 10, 2012

(54) METHODS FOR THE TREATMENT OF HIV-1 RELATED FAT MALDISTRIBUTION, FASTING HYPERLIPIDEMIA AND MODIFICATION OF ADIPOCYTE PHYSIOLOGY

(75) Inventors: Linda M. Pacioretty, Brooktondale, NY (US); John G. Babish, Brooktondale, NY (US)

(73) Assignee: Bionexus, Ltd., Ithaca, NY (US)

( * ) Notice: Subject to any disclaimer, the term of this patent is extended or adjusted under 35 U.S.C. 154(b) by 1096 days.

This patent is subject to a terminal disclaimer.

(21) Appl. No.: 11/821,221

(22) Filed: Jun. 22, 2007

(65) Prior Publication Data

US 2008/0114065 A1 May 15, 2008

Related U.S. Application Data

(63) Continuation-in-part of application No. 10/699,195, filed on Oct. 31, 2003.

(60) Provisional application No. 60/428,246, filed on Nov. 22, 2002.

(51) Int. Cl.
- *A61K 31/19* (2006.01)
- *A61K 31/415* (2006.01)
- *A61K 31/28* (2006.01)
- *A61K 31/20* (2006.01)
- *A61K 31/16* (2006.01)
- *A61K 31/095* (2006.01)

(52) U.S. Cl. ........ 514/557; 514/396; 514/400; 514/505; 514/558; 514/706

(58) Field of Classification Search .................. None
See application file for complete search history.

(56) References Cited

U.S. PATENT DOCUMENTS

| | | | | |
|---|---|---|---|---|
| 6,071,545 | A | * | 6/2000 | Hendler et al. ............... 426/74 |
| 6,365,176 | B1 | * | 4/2002 | Bell et al. ..................... 424/439 |
| 2002/0132219 | A1 | * | 9/2002 | McCleary ..................... 435/1.1 |

OTHER PUBLICATIONS

Hadigan et al., "Metformin in the Treatment of HIV Lipodystrophy Syndrome—A Randomized Controlled Trial," JAMA, Jul. 26, 2000, vol. 284, No. 4; pp. 472-477.*

Domingo et al., "Subcutaneous adipocyte apoptosis in HIV-1 protease inhibitor associated lipodystrophy," AIDS, 1999, vol. 13, No. 16; pp. 2261-2267.*

Kim et al., "Association of anti-obesity activity of N-acetylcysteine with metallothionenin-II down-reugulation," Exp. Mol. Med., 38 (2), pp. 162-172, Apr. 2006.*

Kleinveld et al., "Failure of N-acetylcysteine to reduce low-density lipoprotein oxidizability in healthy subjects," Eur. J. Clin. Pharmacol., 43(6): pp. 639-642 (1992)).*

Larsen et al., "A. Efficacy and safety of dietary supplements containing CLA for the treatment of obesity: evidence from animal and human studies," J. Lipid Res., 2003, 44, pp. 2234-2241.*

* cited by examiner

*Primary Examiner* — Sreeni Padmanabhan
*Assistant Examiner* — Jody Karol

(57) ABSTRACT

Methods for treating or preventing metabolic dysregulation of adipocytes resulting from HIV-1 infection or chronic inflammation are disclosed. The compositions contain a conjugated fatty acid, a thiol-containing compound and a bioavailable form of trivalent chromium.

8 Claims, 14 Drawing Sheets

[A]

Alpha-Pyridine-Carboxylic Acid, Alpha-Pyridine-Carboxylic Acid,

[B]

Beta-Pyridine-Carboxylic Acid, Nicotinic Acid, Niacin, Cr-polynicotinate widely distributed in many natural sources including humans.

[C]

Carnosine; naturally occurring dipeptide

[A]

[B]

METHODS FOR THE TREATMENT OF HIV-1 RELATED FAT MALDISTRIBUTION, FASTING HYPERLIPIDEMIA AND MODIFICATION OF ADIPOCYTE PHYSIOLOGY

CROSS-REFERENCE TO RELATED APPLICATIONS

This application is a continuation-in-part of U.S. application Ser. No. 10/699,195 filed Oct. 31, 2003, which claims the benefit under 35 U.S.C. §119(e) to provisional application No. 60/428,246, filed Nov. 22, 2002, the entirety of which are incorporated herein by reference.

BACKGROUND OF THE INVENTION

1. Field of the Invention

The present invention provides compounds, compositions, kits, and methods comprising drugs, medical foods, and dietary supplements for the prevention and treatment of metabolic disorders, in particular, insulin resistance syndromes, diabetes, obesity, weight gain, hyperlipidemia, fat maldistribution, cardiovascular disease and osteoporosis resulting from general inflammation or HIV-1 infection. More specifically, the invention relates to anti-inflammatory, pharmaceutical compositions and therapeutic methods utilizing such compositions to modify adipocyte physiology to enhance insulin sensitivity.

2. Description of the Related Art

Research has implicated dysregulated inflammatory processes in the pathogenesis of many prevalent, chronic diseases including metabolic syndrome, insulin resistance, diabetes, obesity, dyslipidemia, lipodystrophy and cardiovascular disease. Increased plasma concentrations of tumor necrosis factor alpha (TNFα), interleukin-6 (IL-6), C-reactive protein (CRP) and plasminogen activator inhibitor-1 (PAI-1), which are characteristic of chronic inflammation, are found in varying degrees in all of these pathologies [Dandona, P., et al. Inflammation: the link between insulin resistance, obesity and diabetes. Trends Immunol. 25(1):407, (2004); Dandona, P. Endothelium, inflammation, and diabetes. Curr Diab Rep 2(4):311-315, (2002)]. As such, anti-inflammatory directed treatment modalities have the potential to provide therapeutic or palliative benefits for these conditions.

Insulin resistance is now well recognized as a chronic inflammatory state. The interrelationship between inflammation and inflammatory mediators and the diabetic state, whether insulin dependent or independent, has long been noted. For example, insulin dependent diabetes mellitus (IDDM) is characterized by an initial inflammatory response or cellular infiltration in or around the pancreatic islet cells [Gepts, W. Pathologic anatomy of the pancreas in juvenile diabetes mellitus. Diabetes 14: 619-633, (1965); see also Koliopanos, A., et al., Cyclooxygenase 2 expression in chronic pancreatitis: Correlation with stage of the disease and diabetes mellitus. Digestion 64: 240-247, (2001); and Luo, C., et al., Cellular distribution and contribution of cyclooxygenase (COX)-2 to diabetogenesis in NOD mouse. Cell Tissue Res. 310: 169-175, (2002)].

The concept of inflammation and adipocyte interaction in relation to these metabolic conditions started with a seminal publication by Hotamisligil et al. in 1993, which demonstrated that adipocytes constitutively express the pro-inflammatory cytokine TNFα, and that TNFα expression in the adipocytes of obese animals (ob/ob mouse, db/db mouse and fa/fa Zucker rat) is markedly increased. Further, neutralization of TNFα by soluble TNFα receptor leads to a decrease in insulin resistance in these animals [Hotamisligil G. S., et al. Adipose expression of tumor necrosis factor-alpha: direct role in obesity-linked insulin resistance. Science 259:87-91, (1993)]. These observations provide a link between an increase in the expression and plasma concentration of a pro-inflammatory cytokine and insulin resistance.

Clinical and experimental data developed since 1993 suggest that all major components of the metabolic syndrome including insulin insensitivity and obesity are associated with inflammatory conditions characterized by increased plasma concentrations of pro-inflammatory cytokines such as TNFα, IL-6, C-reactive protein (CRP) and PAI-1 [Yudkin, J. S., et al. C-reactive protein in healthy subjects: associations with obesity, insulin resistance, and endothelial dysfunction: a potential role for cytokines originating from adipose tissue? Arterioscler. Thromb. Vasc. Biol. 19:972-978, (1999); Mohamed-Ali, V., et al. Subcutaneous adipose tissue releases interleukin-6, but not tumor necrosis factor-a, in vivo. Endocrinol. Metab. 82:4196-4200, (1997); Lundgren, C. H., et al. Elaboration of type-1 plasminogen activator inhibitor from adipocytes. A potential pathogenetic link between obesity and cardiovascular disease. Circulation 93:106-110, (1996)]. Clinically, it has been shown that human adipose tissue expresses TNFα constitutively and that expression falls after weight loss [Kern, P. A., et al. The expression of tumor necrosis factor in human adipose tissue. Regulation by obesity, weight loss, and relationship to lipoprotein lipase. J. Clin. Invest. 95:2111-2119, (1995)].

The prevalence of diabetes mellitus has increased roughly in parallel with that of obesity, which has itself doubled in the United States in the last twenty years. Some experts have stated that obesity in the United States is an epidemic. In any case, as the population ages, it is likely that the rate of obesity will increase with time. The correlation between obesity and diabetes is manifest, as are the correlations between cardiovascular disease and both obesity and diabetes. A non-obese, type two diabetic is far more likely to suffer from cardiovascular disease than is a non-obese, non-diabetic; and an obese non-diabetic is at an even higher risk for cardiovascular disease than is a non-obese diabetic. Thus, in addition to inflammation, there are apparently causal links between cardiovascular disease and both obesity and diabetes.

It is now generally accepted that adipose tissue acts as an endocrine organ producing a number of biologically active peptides with an important role in the regulation of food intake, energy expenditure and a series of metabolic processes. Adipose tissue secretes a number of bioactive peptides collectively termed adipokines. Through their secretory function, adipocytes lie at the heart of a complex network capable of influencing several physiological processes (FIG. 1). Dysregulation of adipokine production with alteration of adipocyte mass has been implicated in metabolic and cardiovascular complications of obesity. In obese individuals, excessive production of acylation-stimulating protein (ASP), TNFα, IL-6 or resistin deteriorates insulin action in muscles and liver, while increased angiotensinogen and PAI-1 secretion favors hypertension and impaired fibrinolysis. Leptin regulates energy balance and exerts an insulin-sensitizing effect. These beneficial effects are reduced in obesity due to leptin resistance. Adiponectin increases insulin action in muscles and liver and exerts an anti-atherogenic effect. Further, adiponectin is the only known adipokine whose circulating levels are decreased in the obese state. The thiazolidinedione anti-diabetic drugs increase plasma adiponectin, supporting the idea that adipokine-targeted pharmacology represents a promising therapeutic approach to control type 2 diabetes and cardiovascular diseases in obesity (FIG. 2) [Guerre-Millo, M. Adipose tissue and adipokines: for better or worse. Diabetes Metabolism 30:13-19, (2004)].

Insulin resistance and/or hyperinsulinemia have been postulated to be the cause of the other abnormal metabolic and cardiovascular risk factors that occur in the metabolic syndrome (FIG. 3). These risk factors have been identified as (1) central obesity (including increased visceral fat); (2) a characteristic dyslipidemia that includes an elevated plasma triglyceride, a low plasma high-density lipoprotein (HDL), and a small dense low-density lipoprotein (LDL) cholesterol particle pattern; (3) a procoagulant state made up of elevated plasma fibrinogen and plasminogen activator inhibitor-1; (4) elevated systolic and diastolic blood pressure; (5) hyperuricemia; and (6) microalbuminuria [Lebovitz, H. E., and Banerji, M. A. Insulin resistance and its treatment by thiazolidinediones. Recent Prog Horm Res. 56:265-94, (2001)].

One method for the treatment of insulin resistance is with oral antihyperglycemic agents. Oral antihyperglycemic agents can be classified into six, distinct classes based upon mechanism of action: (1) biguanides, such as metformin, that decrease hepatic glucose production; (2) sulfonylureas such as glipizide, glyburide, and glimepiride, and (3) nonsulfonylureas such as repaglinide and nateglinide that increase pancreatic insulin secretion; (4) α-glucosidase inhibitors, with acarbose being the only representative on the market, that delay intestinal carbohydrate absorption; (5) thiazolidinediones, rosiglitazone and pioglitazone, agents that increase fatty acid uptake of adipocytes as well as glucose uptake in both muscle and fat; and 6) anti-inflammatories (e.g. aspirin (not used due to toxicity associated with the levels necessary to improve glucose control)) [Scheen, A. J. Drug treatment of non-insulin-dependent diabetes mellitus in the 1990s. Achievements and future developments. Drugs 54(3):355-368, (September 1997); Scheen, A. J. and Lefebvre, P. J. Antihyperglycaemic agents. Drug interactions of clinical importance. Drug Saf; 12(1):32-45, (January 1995); Inzucchi, S. E. Oral antihyperglycemic therapy for type 2 diabetes: scientific review. JAMA. 287(3):360-372, (Jan. 16, 2002); and Gao, Z., et al. Aspirin inhibits serine phosphorylation of insulin receptor substrate 1 in tumor necrosis factor-treated cells through targeting multiple serine kinases. J. Bio. Chem. 278(27): 24944-24950, (2003)].

With few exceptions, the available antidiabetic drugs are equally effective at lowering glucose concentrations. Due to their differing mechanisms of action, they appear to have distinct metabolic effects as reflected in their effect on cardiovascular risk and adverse effect profiles. Metformin currently is the only drug associated with weight loss (or no effect on body weight); it has become the most widely prescribed single hyperglycemic drug and is generally regarded as the best first-line agent especially in the obese patient without contraindications for its use.

Failure to maintain adequate blood glucose for extended periods, however, is frequently seen independent of choice of drug. For example, sulphonylureas have a secondary failure rate of up to 10% each year. This associated worsening hyperglycemia often necessitates the use of polypharmacy; i.e. three years after diagnosis, approximately half of patients require more than one pharmaceutical agent and within nine years this increases to 75% of all patients [Turner, R. C., Cull, C. A., Frighi, V., and Holman, R. R. Glycemic control with diet, sulfonylurea, metformin, or insulin in patients with type 2 diabetes mellitus: progressive requirement for multiple therapies (UKPDS 49). UK Prospective Diabetes Study (UKPDS) Group. JAMA. 281(21):2005-2012, (Jun. 2, 1999)].

Moreover, despite the use of combination therapy physicians generally do not reach targets for glycemic control [Zinman, B. PPARgamma agonists in type 2 diabetes: how far have we come in preventing the inevitable'? A review of the metabolic effects of rosiglitazone. Diabetes Obes Metab. 3 Suppl 1:34-43, (August 2001)].

Statistics on the increasing incidence of NIDDM and the rate of therapeutic failures in maintaining adequate blood glucose indicate that new approaches in the treatment of NIDDM and its complications are important public health priorities. Although diet, regular exercise and weight control have proven effective for modifying the pathogenesis of insulin resistance and increasing the efficacy of antidiabetic drugs, it can be anticipated that a majority of persons will eschew dietary modifications and exercise and that monotherapy will ultimately fail to adequately control the myriad of metabolic imbalances manifest in NIDDM. In light of the tremendous cost of NIDDM, both in terms of human suffering and monetary resources, it seems highly desirable to have additional agents to support treatment [McCarty, M. F. Nutraceutical resources for diabetes prevention—an update. Med. Hypotheses. 64(1):151-158, (2005); McCarty, M. F. Toward practical prevention of type 2 diabetes. Med. Hypotheses. 54(5):786-793, (May 2000)].

In addition to diabetes, obesity and cardiovascular disease, other conditions are now recognized as inflammatory pathologies. These include (1) diseases of the digestive organs such as ulcerative colitis, Crohn's disease, pancreatitis and gastritis; (2) proliferative diseases, such as benign tumors, polyps, hereditary polyposis syndrome, colon cancer, rectal cancer, breast cancer, prostate cancer, and stomach cancer; and (3) ulcerous disease of the digestive organs, and (4) cardiovascular pathologies including stenocardia, atherosclerosis, myocardial infarction, sequelae of stenocardia or myocardial infarction, senile dementia, and cerebrovascular diseases. Further, chronic HIV-1 infection is now recognized as an inflammatory pathology related to alterations in glucose and lipid metabolism.

As in the case with many other infections, HIV infection is accompanied by disturbances in lipid and glucose metabolism. These metabolic abnormalities are further confounded by hypercholesterolemia and hypertriglyceridemia induced by anti-retroviral (AR) drugs. It has been estimated that almost two-thirds of HIV/AIDS patients exhibit abnormal fat distribution coincident with AR-therapy (ART). Clinicians have termed this abnormal fat distribution lipodystrophy or fat maldistribution. Although various terms have been used, the term both lipodystrophy and fat maldistribution will be used here interchangeably to describe the syndrome of body shape changes related to changes in fat distribution in people with HIV/AIDS receiving AR-therapy (HIV/ART).

Various descriptions have been proposed for the morphologic abnormalities and the metabolic alterations that appear to be associated with fat maldistribution. While clinicians have a general understanding of changes in fat distribution occurring in persons with HIV, no consensus exists among them on the clinical measures used to define fat maldistribution. When questioned, physicians generally describe a syndrome of "maldistribution of body fat," "buffalo hump," "thinning of arms and legs," "facial thinning," and/or "increases in abdomen size." Few physicians mention metabolic markers when defining fat maldistribution.

"Lipo" refers to fat and "dystrophy" means abnormal growth. Before being recognized in HIV-infected patients, the lipodystrophies were described as rare abnormalities of adipose tissue characterized by body shape changes and metabolic abnormalities, including insulin resistance, hyperglycemia, and hyperlipidemia.

Although there appear to be some similarities between the established lipodystrophies seen prior to HIV and that seen in HIV/ART patients, there is little evidence of fat accumulation or maldistribution as being a common presentation in persons with lipodystrophy before the development of successful ART combinations for HIV. The fat maldistribution with HIV/AR-related lipodystrophy is typically a mix of central fat accumulation and peripheral fat loss, and this pattern does not seem to fit readily into any definition of previously described lipodystrophies.

Historically, before HIV, lipodystrophy was used to describe features of lipoatrophy only. The use of this term to describe features of fat accumulation as well as fat loss in HIV/ART-patients helped to initiate the confusion, which still exists, on the clinical case definition of HIV/ART-related lipodystrophy. Nevertheless, it is now accepted that the lipodystrophy seen in patients with HIV infection receiving ART is a syndrome involving physical and metabolic abnormalities.

The physical changes associated with the HIV/ART lipodystrophy syndrome can be divided into two major types, both of which involve an abnormal or maldistribution of body fat: lipoatrophy or fat wasting and lipohypertrophy or fat accumulation. An increase in abdominal girth is a common complaint in patients, while thinning of the extremities is also frequently seen, often with prominence of the veins in the arms and legs (cabling) due to subcutaneous fat loss. A substantial proportion of patients report increased wrinkling of the skin with a loss of subcutaneous tissue in the cheeks and around the nose and lips.

Abnormal metabolic changes include altered lipid metabolism manifest by increased triglycerides, increased total cholesterol and increased low-density lipoprotein (LDL) cholesterol. Alterations in glucose metabolism with lipodystrophy include insulin resistance, impaired glucose tolerance and NIDDM.

Although surgery is sometimes elected to remove unsightly fat deposits and restore normal facial appearance, the most frequently prescribed drugs for maintaining normal body composition are recombinant human growth hormone (Somatotrophin®) and anabolic steroids (e.g. Oxandrin®). Other adjunctive measures, such as progressive resistance exercises may also be utilized. Cosmetic surgery appears to be only a stopgap measure and patients frequently continue abnormal body fat deposition. The medications described are highly effective in many patient groups. However, human growth hormone is costly and anabolic steroids may present significant hepatic and cardiovascular risk to the HIV patient.

Among the dietary supplements sold to promote body composition changes, N-acetylcysteine (NAC), L-carnitine, acetyl-L-carnitine, arginine and omega-3 fatty acids have been suggested for wasting and lipodystrophy in HIV/AIDS. No positive data have yet been developed to support these recommendations.

The role of NAC in HIV has been examined since 1989 in 16 peer-reviewed publications (Breitkreutz R, et al. *Improvement of immune functions in HIV infection by sulfur supplementation: two randomized trials* [see comments]. J Mol Med 2000; 78(1):55-62; Akerlund B, et al. *N-acetylcysteine treatment and the risk of toxic reactions to trimethoprim-sulphamethoxazole in primary Pneumocystis carinii prophylaxis in HIV-infected patients*. J Infect 1997; 35:143-147; Jahoor F, et al. *Erythrocyte glutathione deficiency in symptom-free HIV infection is associated with decreased synthesis rate*. Am J Physiol 1999; 276:E205-E211; Walmsley S L, et al. *A randomized trial of N-acetylcysteine for prevention of trimethoprim-sulfamethoxazole hypersensitivity reactions in Pneumocystis carinii pneumonia prophylaxis (CTN 057). Canadian HIV Trials Network 057 Study Group*. J Acquir Immune Defic Syndr Hum Retrovirol 1998; 19(5):498-505; Look M P, et al. *Sodium selenite and N-acetylcysteine in antiretroviral-naive HIV-1-infected patients: a randomized, controlled pilot study*. Eur J Clin Invest 1998; 28:389-397; Herzenberg L A, et al. *Glutathione deficiency is associated with impaired survival in HIV disease*. Proc Natl Acad Sci USA 1997; 94:1967-1972; Akerlund B, et al. *Effect of N-acetylcysteine (NAC) treatment on HIV-1 infection: a double-blind placebo-controlled trial*. Eur J Clin Pharmacol 1996; 50:457-461; Witschi A, et al. *Supplementation of N-acetylcysteine fails to increase glutathione in lymphocytes and plasma of patients with AIDS*. AIDS Res Hum Retroviruses 1995; 11:141-143; de Quay B, et al. *Glutathione depletion in HIV-infected patients: role of cysteine deficiency and effect of oral N-acetylcysteine*. AIDS 1992; 6:815-819; De Rosa S C, et al. *N-acetylcysteine replenishes glutathione in HIV infection*. Eur J Clin Invest 2000; 30:915-929; Muller F, et al. *Virological and immunological effects of antioxidant treatment in patients with HIV infection*. Eur J Clin Invest 2000; 905-914; Kinscherf R, et al. *Effect of glutathione depletion and oral N-acetyl-cysteine treatment on CD4+ and CD8+ cells*. FASEB J 1994; 8:448-451; Bogden J D, et al. *Status of selected nutrients and progression of human immunodeficiency virus type 1 infection*. Am J Clin Nutr 2000; 72:809-815; Skurnick J H, et al. *Micronutrient profiles in HIV-1-infected heterosexual adults*. J Acquir Immune Defic Syndr Hum Retrovirol 1996; 12:75-83; Bogden J D, et al. *Micronutrient status and human immunodeficiency virus (HIV) infection*. Ann NY Acad Sci 1990; 587:189-[95]. Due to its history of safe use as a therapeutic, NAC has been suggested as a potential supplement for glutathione replenishment in HIV since 1991 (Droge W, et al. *Modulation of lymphocyte functions and immune responses by cysteine and cysteine derivatives*. Am J Med 1991; 91:140 S-144S; Mihm S, et al. *Inhibition of HIV-1 replication and NF-kappa B activity by cysteine and cysteine derivatives*. AIDS 1991; 5:497-503; Harakeh S, and Jariwalla R J. *Comparative study of the anti-HIV activities of ascorbate and thiol-containing reducing agents in chronically HIV-infected cells*. Am J Clin Nutr 1991; 54:1231S-1235S). While NAC has demonstrated several positive effects for people living with HIV, no research studies have reported that treatment of HIV-infected persons with NAC alone, or in combination with other nutrients or drugs, can successfully ameliorate fat maldistribution or hyperlipidemia.

Research on fatty acids in HIV has been generally limited and only one clinical trial has been reported on HIV wasting and fatty acid supplementation. A combination consisting of omega-3 fatty acids and arginine was clinically tested for its ability to affect weight gain and blood lipid levels in HIV/ART patients (Sudre, P C, et al. *A randomized double-blind controlled study of 6 months of oral nutritional supplementation with arginine and omega-3 fatty acids in HIV-infected patients*. Swiss HIV Cohort Study. 1998 AIDS 12 (1)53-63). Sixty-four HIV-infected outpatients with CD4 counts greater than or equal to 100 µL were randomized to receive 7.4 g arginine plus 1.7 g omega-3 fatty acids or placebo daily. Gain in body weight and fat mass were approximately 2 and 1 kg, respectively in both treatment and placebo groups. Thus, enrichment of an oral nutritive supplement with arginine and omega-3 fatty acids did not improve weight gain or fat-free mass in HIV/ART patients. Such results imply that fatty acid supplementation alone, or in certain obvious combinations, are unlikely to positively affect fat distribution or hyperlipidemia in HIV/ART patients.

Inflammatory mediated metabolic disorders such as fasting hyperlipidemia and fasting hyperglycemia are prevalent among HIV-infected individuals receiving ART. Morphological changes accompany these inflammatory mediated metabolic disorders and have been termed lipodystrophy syndrome. Affected individuals show fat redistribution, such as fat loss (e.g., in face) or fat accumulation (e.g., in abdominal area). These metabolic disorders are generally attributed to ART. Left untreated, the downstream adverse consequences of fat maldistribution include atherogenesis and atherosclerotic vascular disease. Thus, there is a critical need to provide nutritional supplementation to manage these metabolic and morphologic disorders. At this time, there are no safe and efficacious nutritional products that can normalize metabolic or body changes in HIV/ART-patients.

Thus, it is to be expected that effective anti-inflammatory based methods of improving insulin sensitivity will be useful in the treatment, prevention or delay of onset of one or more of the foregoing inflammatory disorders. Dietary based anti-inflammatory compounds and extracts represent an as yet underutilized source for palliative or preventive treatment modalities.

SUMMARY OF THE INVENTION

The disclosed invention is directed to compositions and methods for treating, preventing or normalizing inflammatory mediated lipoatrophy or fat maldistribution, metabolic syndrome, impaired fasting glucose, diabetes, and hyperlipidemia. One embodiment of the disclosed invention comprises (1) a conjugated fatty acid, (2) one member selected from the group consisting of thiol-containing compounds and (3) one member selected from the group consisting of bioavailable forms of trivalent chromium. Advantageously, the conjugated fatty acid is conjugated linoleic acid in the triglyceride form. Preferably, the thiol-containing compound is N-acetyl cysteine, or lipoic acid. Also preferably, the bioavailable form of trivalent chromium is chromium tricarsinoate or chromium carnitine.

Also disclosed herein is: (1) a pharmaceutical composition comprising an HIV-1 protease inhibitor selected from the group comprising saquinavir (Fortovase®), ritonavir (Norvir®), indinavir (Crixivan®), nelfinavir (Viracept®), amprenavir (Agenerase®), lopinavir (Kaletra®), atazanavir (Reyataz®), fosamprenavir (Lexiva®), and tipranavir (Aptivus®), a conjugated fatty acid, one member selected from the group consisting of thiol-containing compounds and one member selected from the group consisting of bioavailable forms of trivalent chromium; and (2) methods of using the composition thereof to modify adipocyte physiology in a subject. Preferably, the protease inhibitor is selected from the group consisting of saquinavir (Fortovase®), ritonavir (Norvir®), indinavir (Crixivan®), nelfinavir (Viracept®), amprenavir (Agenerase®), lopinavir (Kaletra®), atazanavir (Reyataz®), fosamprenavir (Lexiva®), and tipranavir (Aptivus®) or a derivative or a precursor thereof. The present invention relates to the unexpected discovery that combinations of a conjugated fatty acid, a thio-containing compound and a bioavailable form of trivalent chromium and a protease inhibitor inhibit the pro-inflammatory effects of TNFα plus a protease inhibitor on adipocytes by increasing the secretion of adiponectin. Preferred embodiments provide compositions and methods for inhibiting pro-inflammatory responses of adipocytes.

The fatty acids herein may exist as mono-, di-, or triglycerides as well as ethers or other derivatives without loss of activity. Advantageously, the conjugated fatty acid is conjugated linoleic acid in the triglyceride form. Preferably, the thiol-containing compound is N-acetylcysteine, or lipoic acid. Preferred bioavailable forms of trivalent chromium include chromium carnosine, chromium carnitine, chromium carnitinate, chromium arginate, chromium methionate, chromium dinicotinate glycine, or chromium tripicolinate. Additional bioavailable forms of trivalent chromium would be other amino acid or peptide chelates. The compositions are useful for treating, preventing or normalizing lipoatrophy or fat maldistribution and increased serum lipids associated with inflammatory stimulation of adipocytes or therapeutic antiretroviral treatment of HIV-1 infection.

The recited compositions are incorporated into a pharmaceutically effective carrier. The pharmaceutically effective carrier may be a tablet, capsule, liquid, microbead, emulsion, powder, granule, suspension, lotion, syrup elixir or kit.

Certain embodiments of the invention provide a method of inflammation-mediated modification of adipocytes in a subject. The method of treatment includes administering to a subject a therapeutically effective dose of a conjugated fatty acid in combination with a pharmacologically effective dose of at least one member selected from the group consisting of a thiol-containing compound and at least one member selected from the group consisting of a bioavailable form of trivalent chromium or derivates thereof. Preferably, those conjugated fatty acids include conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, and docosapentaenoic acid. Also preferably the thiol containing compounds include cysteine, N-acetylcysteine, lipoic acid, methionine, glutathione, N-(2-mercaptopropionyl)glycine, L-2-oxothiazolidine-4-carboxylate, cysteamine, D-penicillamine, L-cysteine ethyl ester, N,N'-diacetyl-L-cystine, taurine and N-acetyl-methionine. Preferred bioavailable forms of trivalent chromium include chromium chloride, chromium carnosine, chromium picolinate, chromium carnitine, chromium nicotinate, chromium carnitinate, chromium arginate, chromium methionate, chromium dinicotinate glycine, or chromium tripicolinate.

Additional embodiments of the invention provide a method of treating HIV/ART-associated fat maldistribution in a subject. The method of treatment includes administering to a subject a therapeutically effective dose of a conjugated fatty acid or conjugated fatty alcohol in combination with a pharmacologically effective dose of at least one member selected from the group consisting of a thiol-containing compound and at least one member selected from the group consisting of a bioavailable form of trivalent chromium or derivates thereof. Preferably, those conjugated fatty acids or conguated fatty alcohols include conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, docosapentaenoic acid, linoleic alcohol, linolenic alcohol, gamma linolenic alcohol, arachidonic alcohol, mead alcohol, stearidonic alcohol alpha-eleostearic alcohol, eleostearic alcohol, pinolenic alcohol, docosadienic alcohol, docosatetraenoic alcohol, octadecadienoic alcohol, octadecatrienoic alcohol, eicosatetraenoic alcohol, eicosapentaenoic alcohol, docosahexaenoic alcohol, and docosapentaenoic alcohol. Also preferably the thiol containing compounds include cysteine, N-acetylcysteine, lipoic acid, methionine, glutathione, N-(2-mercaptopropionyl)glycine, L-2-oxothiazolidine-4-carboxylate, cysteamine, D-penicillamine, L-cysteine ethyl ester, N,N'-diacetyl-L-cystine, taurine and N-acetyl-methionine. Preferred bioavailable forms of trivalent chromium include chromium chloride, chromium carnosine, chromium picolinate, chromium carnitine, chromium nicotinate, chromium carnitinate, chromium arginate, chromium methionate, chromium dinicotinate glycine, or chromium tripicolinate.

DETAILED DESCRIPTION OF THE INVENTION

Figure 1:
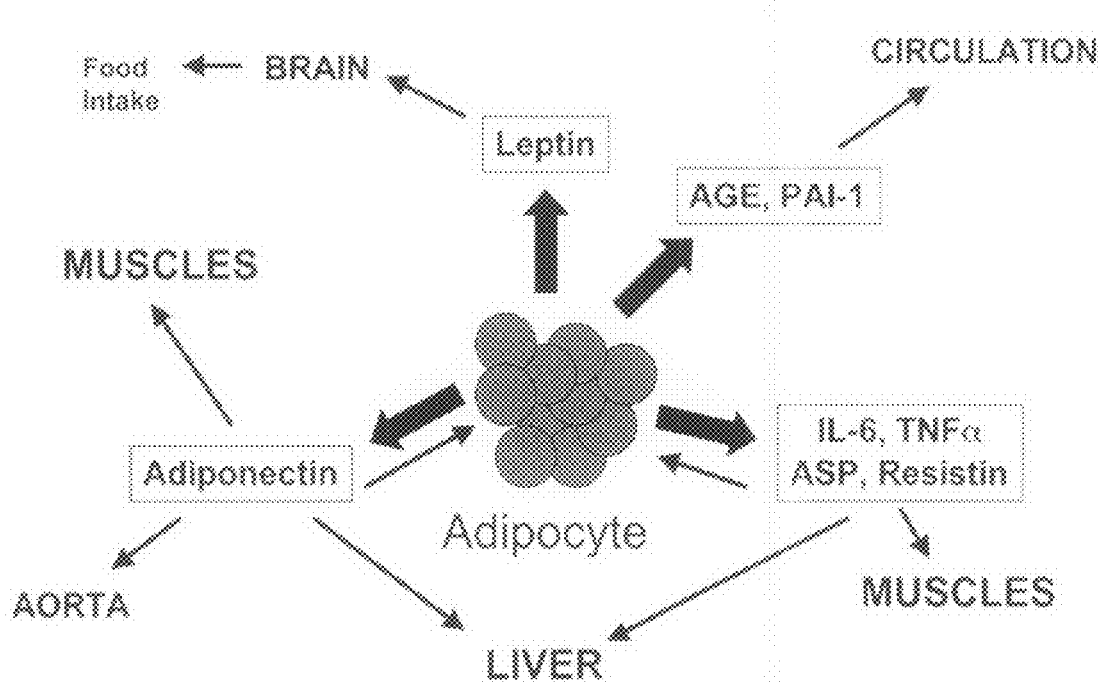
FIG. 1 illustrates the beneficial and deleterious effects of adipose secreted factors implicated in energy homeostasis, insulin sensitivity and vascular homeostasis. Adapted from Guerre-Millo, M. Adipose tissue and adipokines: for better or worse. Diabetes Metabolism 30:13-19, (2004).
Figure 2:
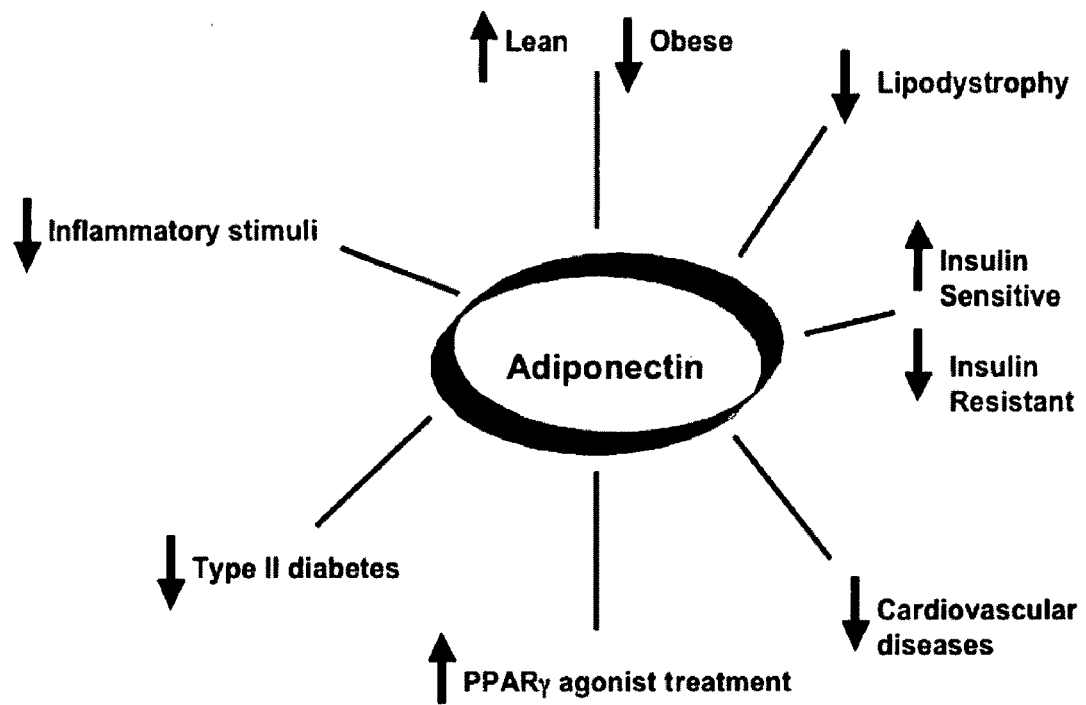
FIG. 2 is a summary of the most important factors and disease states that lead to an up-regulation (upward pointing arrow) or down-regulation (downward pointing arrow) of adiponectin in adipose tissue. Adapted from Trujillo, M. E and Scherer, P. E. Adiponectin—journey from an adipocyte secretory protein to biomarker of the metabolic syndrome. Journal of Internal Medicine 257:167-175, (2005).
Figure 3:
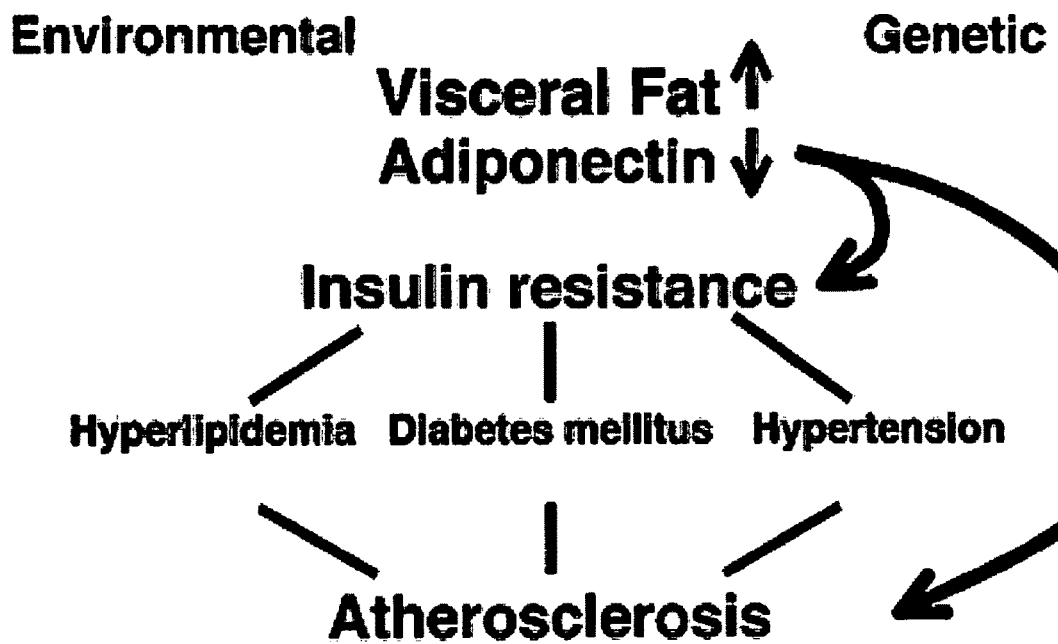
FIG. 3 provides a schematic of the relationship of the pathophysiological components of the metabolic syndrome.

The invention provides compounds, compositions, kits and methods for the treatment of insulin related disorders in a subject. The compositions, compounds, and methods comprise administering to the subject a composition consisting of a conjugated fatty acid, at least one member selected from the group consisting of N-acetyl cysteine and lipoic acid, and at lease one member from the group consisting of chromium carnosine and chromium carnitine, or pharmaceutically acceptable salts or mixtures thereof. The present invention relates to the unexpected discovery that the composition described herein increased adipocyte lipogenesis, and inhibited inflammation-induced lipolysis, IL-6 secretion and the attenuation of adiponectin secretion. Preferred embodiments provide compositions, kits and methods for enhancing adipocyte lipogenesis. Compositions and methods of the invention can also decrease secretion of IL-6 and increase secretion of adiponectin from adipocytes in pro-inflammatory states.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 10th Ed., McGraw Hill Companies Inc., New York (2001).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2 can be 0, 1 or 2 for variables that are inherently discrete, and can be 0.0, 0.1, 0.01, 0.001, or any other real value for variables that are inherently continuous.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or compounds, but may also include additional features or compounds.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used herein, "adipocyte modification" means a change in the physical or physiochemical function of the cell from the cell's state prior to treatment. Nonlimiting examples of physical or physiochemical functional changes include altered rates of secretion or amounts of naturally occurring secreted products, the introduction, production and secretion of novel products, the abrogation of secretion of selected compounds, or physical changes in cell morphology and function which may include alterations in membrane permeability or thickness, modification of cell surface receptor numbers or binding efficiency, or the introduction and expression of novel cell surface receptors. The methods of the invention provide for modification of adipocyte physiology in a subject. While modification of adipocyte physiology to enhance lipogenesis or increase adiponectin secretion is desirable in and of itself, it is to be recognized that a modification of adipocyte physiology can have other salutary effects. The present compositions also reduce the inflammatory response and thereby promote healing of, or prevent further damage to, the affected tissue.

The term "treat" and its verbal variants refer to palliation or amelioration of an undesirable physiological state. Thus, for example, where the physiological state is poor glucose tolerance, "treatment" refers to improving the glucose tolerance of a treated subject. As another example, where the physiological state is obesity, the term "treatment" refers to reducing the body fat mass, improving the body mass or improving the body fat ratio of a subject. Treatment of diabetes means improvement of blood glucose control. Treatment of inflammatory diseases means reducing the inflammatory response either systemically or locally within the body. Treatment of osteoporosis means an increase in the density of bone mineralization or a favorable change in metabolic or systemic markers of bone mineralization. The person skilled in the art will recognize that treatment may, but need not always, include remission or cure.

"Insulin related disorders" refers to those diseases or conditions where the response to insulin is either causative of the disease or has been implicated in the progression or suppression of the disease or condition. Representative examples of insulin related disorders include, without limitation diabetes, diabetic complications, insulin sensitivity, polycystic ovary disease, hyperglycemia, dyslipidemia, insulin resistance, metabolic syndrome, obesity, body weight gain, inflammatory diseases, diseases of the digestive organs, stenocardia, myocardial infarction, sequelae of stenocardia or myocardial infarction, senile dementia, and cerebrovascular dementia. See, *Harrison's Principles of Internal Medicine,* 13th Ed., McGraw Hill Companies Inc., New York (1994). Examples, without limitation, of inflammatory conditions include diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general.

The term "prevent" and its variants refer to prophylaxis against a particular undesirable physiological condition. The prophylaxis may be partial or complete. Partial prophylaxis may result in the delayed onset of a physiological condition. The person skilled in the art will recognize the desirability of delaying onset of a physiological condition, and will know to administer the compositions of the invention to subjects who are at risk for certain physiological conditions in order to delay the onset of those conditions. For example, the person skilled in the art will recognize that obese subjects are at elevated risk for coronary artery disease. Thus, the person skilled in the art will administer compositions of the invention in order to increase insulin sensitivity in an obese, whereby the onset of diabetes mellitus or dyslipemia may be prevented entirely or delayed.

As used herein "diabetic complications" include, without limitation, retinopathy, muscle infarction, idiopathic skeletal hyperostosis and bone loss, foot ulcers, neuropathy, arteriosclerosis, respiratory autonomic neuropathy and structural derangement of the thorax and lung parenchyma, left ventricular hypertrophy, cardiovascular morbidity, progressive loss of kidney function, and anemia.

As used herein, the term "fasting hyperlipidemia" refers to a pathognomic condition manifest by elevated serum concentrations of total cholesterol (>200 mg/dL), LDL cholesterol (>130 mg/dL), or triglycerides (>150 mg/dL) or decreased HDL cholesterol (<40 mg/dL). Further, as used herein, the term "fat" refers to serum and adipose triglyceride content and "triglycerides" refers to triacylglycerol esters of fatty acids.

As used herein, the terms hyperinsulinemia" and "hyperglycemia" refer to a fasting insulin concentration >17 IU/ml) and fasting glucose >125 mg/dL.

As used herein, the term "impaired fasting glucose" refers to fasting serum glucose values greater than 110 mg/dL measured on at least two separate occasions.

As used herein, the term "insulin sensitivity" refers to the ability of a cell, tissue, organ or whole body to absorb glucose in response to insulin. As used in an in vivo context, "insulin sensitivity" refers to the ability of an organism to absorb glucose from the blood stream. An improvement in insulin sensitivity therefore results in an improved ability of the organism to maintain blood glucose levels within a target range. Thus, improved insulin sensitivity may also result in a decreased incidence of hyperglycemia. Improved insulin sensitivity can also treat, prevent or delay the onset of various metabolic conditions, such as diabetes mellitus, syndrome X and diabetic complications. Because of the improved metabolic processing of dietary sugar, improved insulin sensitivity can also treat, prevent or delay the onset of hyperlipidemia and obesity. Additionally, improved insulin sensitivity can lead to treatment, prevention or delayed onset of a variety of inflammatory conditions, such as, for example, diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general.

In regard to improvement of insulin sensitivity, then, a subject may be an animal or human who has been diagnosed with insulin resistance or an animal or human, such as an obese or aged animal or human, which is determined to be at risk for insulin resistance. The ordinary clinician will be able to diagnose insulin resistance and, via analysis of a subject's health history, determine whether the subject is at risk for insulin resistance.

The methods of the present invention are intended for use with any subject that may experience the benefits of the methods of the invention. Thus, in accordance with the invention, "subjects" include humans as well as non-human subject, particularly domesticated animals. It will be understood that the subject to which a compound of the invention is administered need not suffer from a specific traumatic state. Indeed, the compounds of the invention may be administered prophylactically, prior to any development of symptoms. The term "therapeutic," "therapeutically," and permutations of these terms are used to encompass therapeutic, palliative as well as prophylactic uses.

As used herein, "improved secretion," means to increase by at least 3%, the rate of secretion or amount of secretion of the referent compound. The invention further provides a method of improving plasma adiponectin concentrations in a subject, comprising administering to the subject an amount of the compound or composition sufficient to increase adiponectin secretion from adipocytes in the subject.

In general, an increase in plasma adiponectin will result in improved insulin sensitivity resulting in improved glucose metabolism, improved blood lipid profiles, and decreased pro-inflammatory adipokine secretion. A decrease in pro-inflammatory adipokine secretion leads to decreased systemic inflammation and disorders associated with inflammation, such as diabetic complications, obesity, inflammatory diseases of the digestive organs, proliferative diseases of the digestive organs, ulcerous diseases of the digestive organs, stenocardia, myocardial infarction, sequelae of stenocardia, sequelae of myocardial infarction, senile dementia, cerebrovascular dementia, immunological diseases and cancer [Guerre-Millo, M. Adipose tissue and adipokines: for better or worse. Diabetes Metabolism 30:13-19, (2004)].

Figure 6:
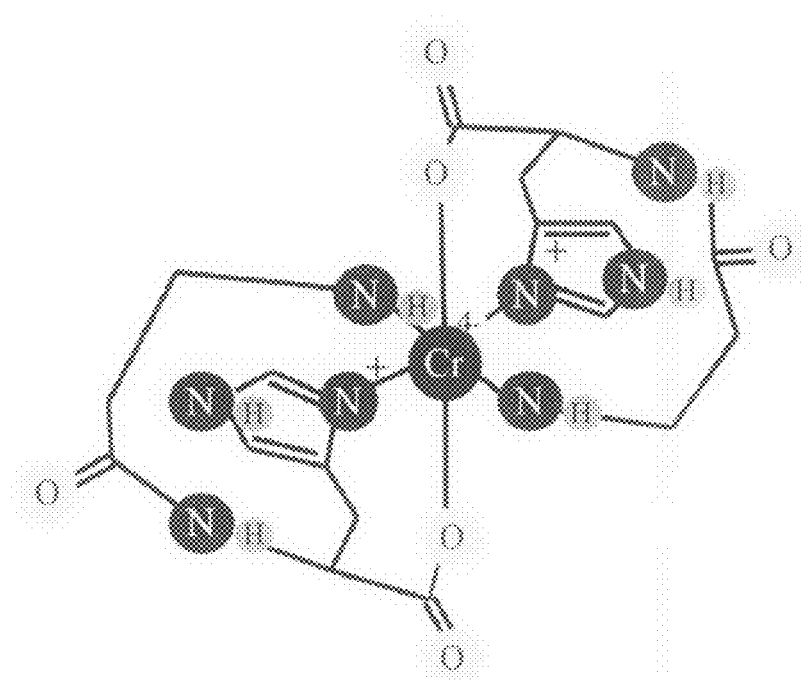
FIG. 6 depicts the [A] di- and [B[ tri-carnosinate structures.
Figure 6:
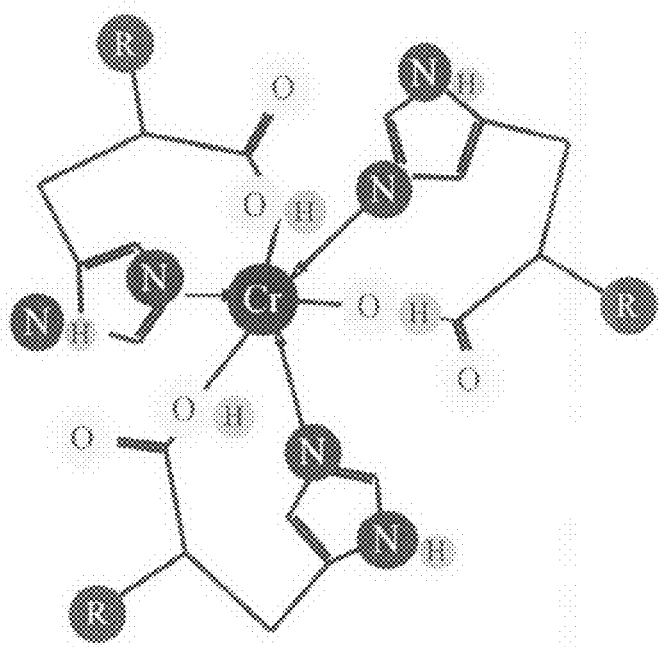

As used herein, "chromium carnosine" refers to a molecular complex consisting of trivalent chromium plus two or three molecules of carnosine or N-β-alanyl-L-histidine (FIG. 6).

In some aspects the compositions further comprise a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. In yet further aspects, the composition additionally comprises one or more members selected from the group consisting of antioxidants, vitamins, minerals, proteins, fats, and carbohydrates.

The term "therapeutically effective amount" is used to denote treatments at dosages effective to achieve the therapeutic result sought. Furthermore, one of skill will appreciate that the therapeutically effective amount of the compound of the invention may be lowered or increased by fine-tuning and/or by administering more than one compound of the invention, or by administering a compound of the invention with another compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined, for example, empirically by starting at relatively low amounts and by step-wise increments with concurrent evaluation of beneficial effect.

The term "pharmaceutically acceptable" is used in the sense of being compatible with the other ingredients of the compositions and not deleterious to the recipient thereof.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, all physical forms are equivalent for the uses contemplated herein and are intended to be within the scope of the present invention.

The compounds according to the invention are optionally formulated in a pharmaceutically acceptable vehicle with any of the well-known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

The compounds of the present invention may be provided in a pharmaceutically acceptable vehicle using formulation methods known to those of ordinary skill in the art. The compositions of the invention can be administered by standard routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, polymers may be added according to standard methodologies in the art for sustained release of a given compound.

The active ingredients of the present invention may also be a combination of anti-HIV-1 therapeutic agents of the protease inhibitor class. The ingredients can be administered in a single formulation or they can be separately administered. Thus, the invention also provides a pharmaceutical pack or kit comprising one or more containers filled with one or more of the ingredients of the compositions of the invention (e.g., capsules or pills containing a conjugated fatty acid, a thio-containing compound, and a bioavailable form of trivalent chromium and at least one member of the group consisting of HIV-1 protease inhibitors. Optionally associated with such container(s) can be a notice in the form prescribed by a government agency regulating the manufacture, use or sale of pharmaceutical products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet.

It is contemplated within the scope of the invention that compositions used to treat a disease or condition will use a pharmaceutical grade compound and that the composition will further comprise a pharmaceutically acceptable carrier. It is further contemplated that these compositions of the invention may be prepared in unit dosage forms appropriate to both the route of administration and the disease and patient to be treated. The compositions may conveniently be presented in dosage unit form be prepared by any of the methods well known in the art of pharmacy. All methods include the step of bringing the active ingredient into association with the vehicle that constitutes one or more auxiliary constituents. In general, the compositions are prepared by uniformly and intimately bringing the active ingredient into association with a liquid vehicle or a finely divided solid vehicle or both, and then, if necessary, shaping the product into the desired composition.

The term "dosage unit" is understood to mean a unitary, i.e. a single dose which is capable of being administered to a patient, and which may be readily handled and packed, remaining as a physically and chemically stable unit dose comprising either the active ingredient as such or a mixture of it with solid or liquid pharmaceutical vehicle materials.

Compositions suitable for oral administration may be in the form of discrete units as capsules, sachets, tablets, soft gels or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, gum arabic, dextran, sodium carboxymethylcellulose, gelatin, methylcellulose and polyvinylpyrrolidone. The active ingredient may also be administered in the form of a bolus, electuary or paste.

Transdermal compositions may be in the form of a plaster, microstructured arrays, sometimes called microneedles, iontophoresis (which uses low voltage electrical current to drive charged drugs through the skin), electroporation (which uses short electrical pulses of high voltage to create transient aqueous pores in the skin), sonophoresis (which uses low frequency ultrasonic energy to disrupt the stratum corneum), and thermal energy (which uses heat to make the skin more permeable and to increase the energy of drug molecules), or via polymer patch.

Compositions suitable for ophthalmic administration may be in the form of a sterile aqueous preparation of the active ingredients, which may be in microcrystalline form, for example, in the form of an aqueous microcrystalline suspension. Liposomal compositions or biodegradable polymer systems may also be used to present the active ingredient for ophthalmic administration.

Compositions suitable for topical or ophthalmic administration include liquid or semi-liquid preparations such as liniments, lotions, gels, and oil-in-water or water-in-oil emulsions such as creams, ointments or pastes; or solutions or suspensions such as drops.

In addition to the compositions described above, the compositions of the invention may also be formulated as a depot preparation. Such long-acting compositions may be administered by implantation (e.g. subcutaneously, intraabdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin.

For systemic treatment according to the present invention, daily doses of from 0.001-200 mg/kg body weight, preferably from 0.002-20 mg/kg of body weight, for example 0.003-10 mg/kg of the combination are administered, corresponding to a daily dose for an adult human of from 0.2 to 14000 mg of the active ingredients. In the topical treatment of dermatological disorders, ointments, creams or lotions containing from 0.1-750 mg/g, and preferably from 0.1-500 mg/g, of the combination may be administered. For topical use in opthalmological ointments, drops or gels containing from 0.1-750 mg/g, and preferably from 0.1-500 mg/g, of the formulation are administered. Oral compositions are formulated, preferably as tablets, capsules, or drops, containing from 0.05-250 mg, preferably from 0.1-1000 mg, of the formulation per dosage unit.

The compounds of this invention either alone or in combination with each other or other compounds generally will be administered in a convenient composition. The following representative composition examples are illustrative only and are not intended to limit the scope of the present invention. In the compositions that follow, "active ingredient" means a compound of this invention.

As used herein, "regulating insulin levels or sensitivity" refers to means for maintaining insulin levels at a particular value or inducing a desired change (either increasing or decreasing) in the level of insulin or in the response to endogenous or exogenous insulin.

As used herein, "therapeutically effective time window" means the time interval wherein administration of the compounds of the invention to the subject in need thereof reduces or eliminates the deleterious effects or symptoms. In a preferred embodiment, the compound of the invention is administered proximate to the deleterious effects or symptoms.

As used herein, the term "CLA isomers" refers to fatty acids (or alcohols) with the same 18-carbon, polyunsaturated structure. In the case of CLA, each isomer is derived from the 18-carbon essential polyunsaturated fat linoleic acid (18:2n-6), which has two cis-double bonds at carbons 9 and 12. CLA isomers also have two double bonds, but they are adjacent to one another, or conjugated, on carbons 7 to 13, and can be cis or trans.

The term "conjugated compound" refers to a compound having at least a portion that is a hydrocarbon, with at least three consecutive carbon-carbon bonds, such that single and double carbon-carbon bonds are found in an alternating manner. Thus, the compound will include the subunit —HC=CH—H$_2$C=CH—. Two preferred categories of conjugated compounds are fatty acids and fatty alcohols. It should be noted that these di- or poly-unsaturated compounds are referred to herein using the common names of the corresponding naturally occurring compounds having the same number of carbons and unsaturations. Although such naturally occurring compounds are not necessarily conjugated, due to the arrangement of their carbon-carbon double bonds, it will be understood in the context of the present invention that only conjugated versions of those compounds are contemplated; i.e., the arrangement of the double bounds will be such that they contain the substructure —C=C—C=C. While compounds having as few as 4, 5, 6, or 7 carbon atoms are contemplated, the preferred conjugated compounds have 8, 9, 10, 12, 14, 16 or more carbon atoms, preferably not more than 32, 30, 28, or 26 carbon atoms.

It should be noted that the phrase "conjugated fatty acid" or "conjugated fatty alcohol", as used herein, also includes isomers of fatty acids and fatty alcohols, as well as any other polyunsaturated compounds. Suitable conjugated fatty acids include, without limitation, conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, docosapentaenoic acid, and all other diunsaturated and polyunsaturated fatty acids. In a preferred embodiment, the conjugated fatty acid is CLA in the triglyceride form.

As used herein, the phrase "conjugated fatty alcohols" includes, without limitation, conjugated versions of linoleic alcohol, linolenic alcohol, gamma linolenic alcohol, arachidonic alcohol, mead alcohol, stearidonic alcohol alpha-eleostearic alcohol, eleostearic alcohol, pinolenic alcohol, docosadienic alcohol, docosatetraenoic alcohol, octadecadienoic alcohol, octadecatrienoic alcohol, eicosatetraenoic alcohol, eicosapentaenoic alcohol, docosahexaenoic alcohol, docosapentaenoic alcohol, and all other diunsaturated and polyunsaturated fatty alcohols. The present invention further includes the use of other conjugated compounds having at least 4, 5, 6, 7, or 8 carbon atoms, that function synergistically with at least one sulfur-containing compound and at least one form of trivalent chromium to promote visceral fat loss, enhance subcutaneous fat deposition, and decrease serum lipids in HIV/ART. Note that the present invention includes alcohols and acids in which one or more of the double bonds result in a cis isomer, as well as those in which one or more of the double bonds result in a trans isomer. In some cases, all the double bonds are cis, while in they are all trans, and in still other cases, they are mixed cis and trans compounds.

CLA occurs naturally in the milk and fat of ruminants. In cattle, CLA is synthesized from dietary linoleic acid by symbiotic bacteria in the bovine rumen. CLA can also be made from linoleic acid during food processing, including cheese making, deep-frying and the manufacture of hydrogenated vegetable oils. However, the majority of CLA in the diet comes from dairy products. CLA supplements are generally produced from linoleic acid from sunflower, soybean and safflower oil. Commercially, CLA may be purchased from Loders Croklaan Lipid Nutrition of Channahon, Ill.

Thiol Compounds—NAC is a metabolite of cysteine, which is classified as a conditionally essential amino acid. Unlike cysteine, NAC is not found in foods but serves as a delivery form of cysteine. The acetyl-substituted amino group of NAC makes the molecule more stable against oxidation than cysteine alone and more bioavailable. As a source of thiol (S—) groups, NAC is converted in the body into metabolites capable of stimulating glutathione (GSH) synthesis, promoting detoxification, and acting directly as a free radical scavenger.

There are no known contraindications to NAC used for nutritional supplementation. Gastrointestinal distress is the most common complaint with oral NAC supplementation; this is generally manifest as nausea, vomiting and diarrhea. Other reactions reported with NAC are general and include headache, and rashes. Rarely, cysteine renal stones will occur (Kelly G S. *Clinical applications of N-acetylcysteine*. Altern Med Rev 1998; 3:114-127).

α-Lipoic acid (ALA), also known as thioctic acid, is a disulfide compound that is a cofactor in ATP-generating reactions in the mitochondria. It is synthesized endogenously in the mitochondria from octanoic acid and L-cysteine. Metabolic reactions in which ALA participates occur in the mitochondria and include the oxidation of pyruvic acid and the oxidation of alpha-ketoglutarate. It is also a cofactor for the oxidation of branched-chain amino acids (leucine, isoleucine and valine) via the branched-chain alpha-keto acid dehydrogenase enzyme complex.

ALA is both a dietary supplement and a drug. Branded products are available in US drug and discount stores, while in Germany ALA is classified as a drug that is approved to treat diabetic polyneuropathy and liver disorders. As a drug, ALA is manufactured for oral and parenteral use. In the treatment of diabetic neuropathy, 300 mg ALA are taken daily in divided doses.

HIV-patients use ALA generally: (1) to protect the liver, (2) to treat peripheral neuropathy, (3) to treat lipodystrophy, and (4) to slow down HIV replication (Jain, R G. et al. *Metabolic complications associated with antiretroviral therapy*. 2001 Antiviral Res 51(3), 151-77). There exists clinical data to support the use of ALA to treat various forms of liver damage (Brinkmann, W. et al. [*Is the rebound effect in liver diseases following glucocorticoid therapy avoidable by using alpha-lipoic acid?*]. 1971 Ther Ggw 110 (12); Bustamante, J. et al. *Alpha-lipoic acid in liver metabolism and disease*. 1998 Free Radic Biol Med 24(6), 1023-39) and glucose utilization in diabetes (Strokov, I, et al. *The function of endogenous protective systems in patients with insulin-dependent diabetes mellitus and polyneuropathy: effect of antioxidant therapy*. 2000 Bull Exp Biol Med 130(10), 986-90). However, no studies have been performed in HIV-patients for these indications. The use of ALA for lipodystrophy and HIV replication have no published clinical support (Patrick, L. *Nutrients and HIV: part three-N-acetylcysteine, alpha-lipoic acid, L-glutamine, and L-carnitine*. 2000 Altern Med Rev 5(4), 290-305). Based upon its known metabolic actions and published clinical trials, it is unlikely that ALA could function independently to affect fat maldistribution or hyperlipidemia in HIV/ART.

There are no known contraindications to ALA used as a supplement. Formal drug interaction studies have not been performed. Based upon pharmacological studies, there was some concern that ALA might potentiate the effects of insulin. However, this potenitation of insulin has not been noted in clinical trials lasting as long as six months with doses of 1800 mg ALA daily (Ziegler, D. et al. *Treatment of symptomatic diabetic polyneuropathy with the antioxidant alpha-lipoic acid: a 7-month multicenter randomized controlled trial (ALADIN III Study). ALADIN III Study Group. Alpha-Lipoic Acid in Diabetic Neuropathy*. 1999 Diabetes Care 22(8), 1296-301).

It is believed that most of the physiological effects of ALA are due to its antioxidant activity. In the recycling of GSH, ALA functions mimic those of NAC as increasing GSH concentrations. Overall, ALA effects parallel those of NAC quite closely, with ALA exhibiting a greater potency in the ability to protect the liver, inhibit HIV replication and increase GSH concentrations.

Neither NAC, ALA nor any other thiol-containing compound has ever been reported to effectively modify fat maldistribution or reduce elevated serum lipids resulting from HIV/ART.

Preferred thiol compounds for combinations with conjugated fatty acids or conjugated fatty alcohols in the present invention include cysteine, N-acetylcysteine, lipoic acid, methionine, glutathione, N-(2-mercaptopropionyl)glycine, L-2-oxothiazolidine-4-carboxylate, cysteamine, D-penicillamine, L-cysteine ethyl ester, N,N'-diacetyl-L-cystine, taurine and N-acetyl-methionine. These compounds may be purchased commercially from Sigma (St. Louis, Mo.) or Garden State Nutritionals (West Caldwell, N.J.).

Bioavailable Trivalent Chromium—The mineral element chromium is viewed with mixed opinions. Although chromium is accepted as nutritionally essential for animals and humans, an understanding of the mechanism of its biological action and the amount of chromium needed for health and optimal function remains elusive. Because there are insufficient appropriate biochemical measures of chromium nutritional status and of the content and the bioavailability of chromium from food, there is a paucity of information that describes who would benefit from increased dietary chromium.

Chromium has been sold as a "fat burner" and is said to help build muscle tissue. However, studies evaluating its effects on weight loss are mostly negative (Grant, K E, et al. *Chromium and exercise training: effect on obese women*. 1997 Med Sci Sports Exerc 29:992-998; Trent, L K, and Thieding-Cancel D. *Effects of chromium picolinate on body composition*. 1995 J Sports Med Phys Fitness 35:273-280; Clarkson, S P, *Effects of exercise on chromium levels. Is supplementation required?* 1997 Sports Med. 23:341-349). Additional studies evaluating its benefits as a performance enhancer or aid to bodybuilding have yielded almost entirely negative results (Clarkson, P M, Effects of exercise on chromium levels. *Is supplementation required?* 1997 Sports Med 23:341-349; Joseph, L J O, et al. *Effect of resistance training with or without chromium picolinate supplementation on glucose metabolism in older men and women*. 1999 Metabolism 48:546-553; Lefavi, R G, et al. *Efficacy of chromium supplementation in athletes: emphasis on anabolism*. 1992 Int J Sport Nutr 2:111-122; Clancy, S P et al. *Effects of chromium picolinate supplementation on body composition, strength, and urinary chromium loss in football players*. 1994 Int J Sport Nutr 4:142-153; Hallmark, M A et al. *Effects of chromium and resistive training on muscle strength and body composition*. 1996 Med Sci Sports Exerc 28:139-144). Weak and contradictory evidence suggests that chromium may lower cholesterol and triglyceride levels (Mertz, W. *Chromium in human nutrition: a review*. 1993 J. Nutr 123:626-633; Press, R I, et al. *The effect of chromium picolinate on serum cholesterol and apolipoprotein fractions in human subjects*. 1990 West J. Med. 152:41-45). Thus, chromium per se does not promote beneficial changes in body composition in humans. The US Federal Trade Commission emphasized this conclusion by ruling in July 1997 (United States of America before Federal Trade Commission, Docket No. C-3758) that there is no basis for claims that the trivalent form of chromium as chromium picolinate promotes weight loss and fat loss in humans.

Prior art reveals a complex composition containing chromium is proposed for the treatment of lipodystrophy syndrome. U.S. Pat. No. 6,365,176 describes a nutritional supplement for lipodystrophy in patients with type 2 diabetes mellitus. The supplement comprises a low-glycemic index carbohydrate source, a source of protein, a source of fat, a source of sterol and/or stanol, a source of chromium, a source of salicylic acid and a source of ginseng. Additionally, the composition may further comprise from about 0.1 to 20 g of N-acetylcysteine. In one embodiment, it is proposed that the nutritional supplement can be administered to HIV-infected individuals to prevent and/or treat metabolic disorders associated with lipodystrophy, such as insulin resistance, atherogenesis and cardiovascular disease as well as fat redistribution. Moreover, U.S. Pat. No. 6,365,176 teaches that the use of chromium and N-acetylcysteine in combination with a sterol or stanol, salicylic acid and ginseng are necessary for the treatment of fat maldistribution or hyperlipidemia in HIV/ART persons. Since sterols or stanols reduce serum cholesterol by interfering with the absorption of dietary cholesterol, they may also negatively affect the absorption of ART, which are for the most part fat-soluble compounds. Such combinations would be contraindicated in HIV/ART.

Additional prior art discloses the use of combinations of chromium and CLAs for type 2 diabetes, improving insulin sensitivity, reducing hypercholesterolemia and reducing body fat. McCarty suggests the use of bioactive chromium for skeletal muscle insulin resistance and CLA for adipocyte insulin resistance (McCarty, M F, *Toward a wholly nutritional therapy for type 2 diabetes*. 2000 Med Hypothesis 54(3):483-487). Similarly, U.S. patent application Ser. No. 09/957,876 filed Sep. 20, 2001 proposes methods and compositions for the treatment of diabetes, improvement of insulin sensitivity, weight loss, reduction of body fat, as well as reduction of hyperglycemia and hypercholesterolemia. The compositions include a chromium complex and a conjugated fatty acid or conjugated fatty alcohol. Both of these disclosures differ from the present invention in that the compositions provided herein do not function to reduce body weight or indiscriminately reduce body fat. Since wasting, or loss of body weight, is a constant concern in HIV patients, formulations that would cause a loss of body weight would be contraindicated. Further, the process of reversing fat maldistribution as seen in HIV/ART requires subcutaneous fat deposition in concert with visceral fat loss—a process not consistent with general fat loss. With respect to the composition, 09/957,876 does not include mono-, di-, or triglycerides of the fatty acids as described herein. Finally, the compositions of the present invention are directed to methods for the treatment of a disorder resulting from the interaction of an infectious agent and therapy against that infectious agent.

A certain embodiment provides a composition comprising about 0.05 to 20 g of conjugated fatty acids or conjugated fatty alcohols per day, about 0.05 to 20 g thiol per day, and about 0.025 to 2 mg of bioavailable, trivalent chromium per day. In the preferred embodiment, the thiol component is decreased from 0.25 to 1.25 mg for every μg of bioavailable, trivalent chromium added. Preferably, the ratio of the conjugated fatty acid or conjugated fatty alcohols to bioavailable, trivalent chromium compound is in the range of 1:25 to 1:800,000 (w/w). More preferably, the ratio of the conjugated fatty acid or conjugated fatty alcohols to bioavailable, trivalent chromium compound (w/w) is 1:45,000 (w/w).

The preferred embodiments include delivering an effective amount of conjugated fatty acids or conjugated fatty alcohols. The preferred conjugated fatty acid is a member selected from the group consisting of linoleic acid (c9,t11), linoleic acid (t10,c12), alpha-linolenic acid, gamma-linolenic acid, arachidonic acid, mead acid, stearidonic acid, alpha-eleostearic acid, eleostearic acid, pinolenic acid, docosadienic acid, docosatetraenoci acid, octadecadienoic acid, octadecatrienoic acid, eicosatetraenoic acid, eicosapentaenoic acid, docosahexaenoic acid, docosapentaenoic acid, linoleic acid, and dihomo-gamma-linoleic acid. Preferred members of the group of conjugated fatty alcohols include linoleic alcohol, linolenic alcohol, gamma-linolenic alcohol, arachidonic alcohol, mead alcohol, stearidonic alcohol, alpha-eleostearic alcohol, eleostearic alcohol, pinolenic alcohol, docosadienic alcohol, docosatetraenoic alcohol, octadecadienoic alcohol, eicosatetraenoic alcohol, eicosapentaenoic alcohol, docosahexaenoic alcohol, and docosapentaenoic alcohol. Of the species listed, those containing two asterisks (**) are particularly preferred. Commercially, the most preferred conjugated fatty acids are available from Loders Croklaan Lipid Nutrition of Channahon, Ill.

The preferred thiol source is a member selected from the group consisting of cysteine, N-acetylcysteine, lipoic acid, methionine, glutathione, N-(2-mercaptopropionyl) glycine, L-2-oxothiazolidine-4-carboxylate, cysteamine, D-penicillamine, L-cysteine ethyl ester, N,N'-Diacetyl-L-cystine, taurine and N-acetyl-methionine. Of the species listed, those containing two asterisks (**) are particularly preferred. Commercially, thiol-compounds are available from Sigma (St. Louis, Mo.).

The preferred bioavailable, trivalent chromium source is a member selected from the group consisting of chromium chloride, chromium carnosine**, chromium picolinate, chromium carnitine*, chromium nicotinate*, chromium carnitinate, chromium arginate, chromium methionate, chromium dinicotinate glycine*, or chromium tripicolinate. Of the species listed, those containing at least one asterisk (*) are preferred and those containing two asterisks (**) are particularly preferred. Commercially, bioavailable trivalent forms of chromium are available from FutureCeuticals of Santa Rosa, Calif.

Preferably, a daily dose of the present composition would be formulated to deliver about 0.05 to 20 g of conjugated fatty acids or conjugated fatty alcohols per day, about 0.05 to 20 g thiol per day, and about 0.025 to 2 mg of bioavailable, trivalent chromium per day.

More preferably, an effective daily dose of the present composition would be formulated to deliver about 0.5 to 15 g of conjugated fatty acids or conjugated fatty alcohols per day, about 0.5 to 15 g thiol per day, and about 0.1 to 1 mg of bioavailable, trivalent chromium per day. Most preferably, an effective daily dose of the present composition would be formulated to deliver about 1 to 10 g of conjugated fatty acids or conjugated fatty alcohols per day, about 1 to 10 g thiol per day, and about 0.2 to 0.6 mg of bioavailable, trivalent chromium per day.

Further Ingredients—The formulation can also contain other ingredients such as one or a combination of other vitamins, minerals, antioxidants, fiber and, other nutritional supplements. Selection of one or several of these ingredients is a matter of formulation design, consumer and end-user preference. The amount of these ingredients added to the nutritional supplements of this invention are readily known to the skilled artisan and guidance to such amounts can be provided by the RDA (Recommended Dietary Allowance) and DRI (Dietary Reference Intake) doses for children and adults. Vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacin amide; zinc sulfate or oxide; calcium pantothenate; copper gluconate; riboflavin; beta-carotene; pyridoxine hydrochloride; thiamin mononitrate; folic acid; biotin; potassium iodide; selenium; sodium selenate; sodium molybdate; phylloquinone; Vitamin $D_3$; cyanocobalamin; sodium selenite; copper sulfate; Vitamin A; Vitamin E; vitamin $B_6$ and hydrochloride thereof; Vitamin C; inositol; Vitamin $B_{12}$; and potassium iodide.

The amount of other additives per unit serving are a matter of design and will depend upon the total number of unit servings of the nutritional supplement daily administered to the patient. The total amount of other ingredients will also depend, in part, upon the condition of the patient. Preferably, the amount of other ingredients will be a fraction or multiplier of the RDA or DRI amounts. For example, the nutritional supplement will comprise 50% RDI (Reference Daily Intake) of vitamins and minerals per unit dosage and the patient will consume two units per day.

Flavors, coloring agents, spices, nuts and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the nutritional supplement contains berry or other fruit flavor. The food compositions may further be coated, for example with a yogurt coating if it is as a bar.

Emulsifiers may be added for stability of the final product. Examples of suitable emulsifiers include, but are not limited to, lecithin (e.g., from egg or soy), or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial sweeteners, e.g., glucose, sucrose, fructose, saccharides, cyclamates, aspartamine, sucralose, aspartame, acesulfame K, or sorbitol.

Manufacture of the Preferred Embodiments—The nutritional supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, soda, starch, vegetable oils, salt solutions, hydroxymethyl cellulose, carbohydrate. In a preferred embodiment, the nutritional supplements may be formulated as powders, for example, for mixing with consumable liquids, such as milk, juice, sodas, water or consumable gels or syrups for mixing into other nutritional liquids or foods. The nutritional supplements of this invention may be formulated with other foods or liquids to provide pre-measured supplemental foods, such as single serving beverages or bars, for example.

In a particularly preferred embodiment, the nutritional supplement will be formulated into a nutritional beverage, a form that has consumer appeal, is easy to administer and incorporate into one's daily regimen, thus increasing the chances of patient compliance. To manufacture the beverage, the ingredients are dried and made readily soluble in water. For the manufacture of other foods or beverages, the ingredients comprising the nutritional supplement of this invention can be added to traditional formulations or they can be used to replace traditional ingredients. Those skilled in food formulating will be able to design appropriate foods or beverages with the objective of this invention in mind.

The nutritional supplement can be made in a variety of forms, such as puddings, confections, (i.e., candy), nutritional beverages, ice cream, frozen confections and novelties, or non-baked, extruded food products such as bars. The preferred form is a powder to add to a beverage or a non-baked extruded nutritional bar. In another embodiment, the ingredients can be separately assembled. For example, certain of the ingredients (e.g., the conjugated fatty acids or alcohols and thiol compounds) can be assembled into a tablet or capsule using known techniques for their manufacture. The remaining ingredients can be assembled into a powder or nutritional bar. For the manufacture of a food bar, the dry ingredients are added with the liquid ingredients in a mixer and mixed until the dough phase is reached; the dough is put into an extruder and extruded; the extruded dough is cut into appropriate lengths; and the product is cooled. The two assembled forms comprise the nutritional supplement and can be packaged together or separately, such as in the form of a kit, as described below. Further, they can be administered together or separately, as desired.

Use of Preferred Embodiments—The preferred embodiments contemplate treatment of insulin related disorder selected from the group consisting of diabetes, diabetic complications, insulin sensitivity, hyperglycemia, dyslipidemia, insulin resistance, metabolic syndrome, obesity and body weight gain. A pharmaceutically acceptable carrier may also be used in the present compositions and formulations.

The preferred embodiments are directed to the treatment of human beings the to treat an insulin related disorder selected from the group consisting of diabetes, diabetic complications, insulin sensitivity, hyperglycemia, dyslipidemia, insulin resistance, metabolic syndrome, obesity and body weight gain. Administration can be by any method available to the skilled artisan, for example, by oral, transmucosal, or parenteral routes. The composition and nutritional supplements of the invention are intended to be orally administered daily. Based on the serving size of 15-20 g powder in 8 oz. water, the recommended dosage is once daily. For example, if the supplement is in the form of a beverage or food bar, then the patient would consume the composition after or during the largest meal. The recommended daily amounts of each ingredient, as described above, serve as a guideline for formulating the nutritional supplements of this invention. The actual amount of each ingredient per unit dosage will depend upon the number of units daily administered to the individual in need thereof. This is a matter of product design and is well within the skill of the nutritional supplement formulator.

The ingredients can be administered in a single formulation or they can be separately administered. For example, it may be desirable to administer the conjugated fatty acids or alcohols and thiol compounds in a form that masks their taste (e.g., capsule or pill form) rather than incorporating them into the nutritional composition itself (e.g., powder or bar). Thus, the invention also provides a pharmaceutical pack or kit comprising one or more containers filled with one or more of the ingredients of the nutritional compositions of the invention (e.g., nutritional supplement in the form of a powder and capsules containing conjugated fatty acids and thiol compounds). Optionally associated with such container(s) can be a notice in the form prescribed by a government agency regulating the manufacture, use or sale of pharmaceutical products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet.

The preferred embodiments provide compositions and methods to promote fat redistribution or decrease fasting hyperlipidemia in HIV/ART subjects. In one embodiment, the composition comprises a first component selected from the group consisting of conjugated fatty acids and one member selected from each of the two groups consisting of thiol compounds and bioavailable trivalent chromium compounds. Preferably, the conjugated fatty acid is conjugated linoleic acid. More preferably, the conjugated linoleic acid isomers c9,t11 and t10,c12 exists in a 50:50 ratio. Preferred components from the thiol group of compounds include N-acetyl-cysteine, lipoic acid, taurine, N-acetylmethionine or glutathione, while preferred components of the bioavailable, trivalent chromium compounds are chromium tricarnosinate, chromium carnitine, and chromium dinicotinate glycine. Most preferably, the thiol compound is N-acetylcysteine or lipoic acid. Most preferred component of the bioavailable, trivalent chromium compounds is chromium tricarnosinate.

In some aspects of this embodiment of the invention, the compositions are useful for adipocyte modification for the improved secretion of adiponectin or, as in other aspects, the modification of adipocyte physiology. In still other aspects of this embodiment the adipocyte modification is a decrease in the secretion of free fatty acids or IL-6.

A first embodiment of the invention provides compositions for the treatment of insulin related disorders in a subject in need. These compositions comprise a therapeutically effective amount of a pharmaceutically acceptable CLA composition comprising a conjugated fatty acid or conjugated fatty alcohol, at least one member selected from the group consisting of thiol-containing compounds and at least one member selected from the group consisting of an amino acid chelate of trivalent chromium.

In further aspects of the embodiment, the compositions are used to treat an insulin related disorder selected from the group consisting of diabetes, diabetic complications, insulin sensitivity, hyperglycemia, dyslipidemia, insulin resistance, metabolic syndrome, obesity and body weight gain.

Compositions of this embodiment may further comprises a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. Additional compositions may further comprise one or more members selected from the group consisting of antioxidants, vitamins, minerals, proteins, fats, and carbohydrates.

The compounds of this invention either alone or in combination with each other or other compounds generally will be administered in a convenient composition. The following representative composition examples are illustrative only and are not intended to limit the scope of the present invention. In the compositions that follow, "active ingredient" means a compound of this invention.

A further embodiment of the invention discloses methods for the treatment of insulin related disorders in a subject in need, this method comprising administering to the subject a composition comprising a therapeutically effective amount of a pharmaceutically acceptable CLA formulation comprising a conjugated fatty acid or conjugated fatty alcohol, at least one member selected from the group consisting of thiol-containing compounds and at least one member selected from the group consisting of an amino acid chelate of trivalent chromium.

In some aspects of this embodiment, the adipocyte modification is the improved secretion of adiponectin while in other aspects the modification is a modification of adipocyte physiology. In yet other aspects, the adipocyte modification results in the decreased secretion of fatty acids and IL-6 and an increased secretion of adiponectin.

In aspects of this embodiment, the insulin related disorder is selected from the group consisting of diabetes, diabetic complications, insulin sensitivity, hyperglycemia, dyslipidemia, insulin resistance, metabolic syndrome, obesity, redistribution of body weight and body weight gain.

In other aspects of this embodiment, the composition further comprises a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. In additional aspects, compositions further comprise one or more members selected from the group consisting of antioxidants, vitamins, minerals, proteins, fats, and carbohydrates.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Increased Lipogenesis in 3T3-L1 Adipocytes Elicited by a CLA Formulation and Components The Model—The 3T3-L1 murine fibroblast model is used to study the potential effects of compounds on adipocyte differentiation and adipogenesis. This cell line allows investigation of stimuli and mechanisms that regulate preadipocytes replication separately from those that regulate differentiation to adipocytes [Fasshauer, M., Klein, J., Neumann, S., Eszlinger, M., and Paschke, R. Hormonal regulation of adiponectin gene expression in 3T3-L1 adipocytes. Biochem Biophys Res Commun, 290: 1084-1089, (2002); Li, Y. and Lazar, M. A. Differential gene regulation by PPARgamma agonist and constitutively active PPARgamma2. Mol Endocrinol, 16: 1040-1048, (2002)] as well as insulin-sensitizing and triglyceride-lowering ability of the test agent [Raz, I., Eldor, R., Cernea, S., and Shafrir, E. Diabetes: insulin resistance and derangements in lipid metabolism. Cure through intervention in fat transport and storage. Diabetes Metab Res Rev, 21: 3-14, (2005)].

As preadipocytes, 3T3-L1 cells have a fibroblastic appearance. They replicate in culture until they form a confluent monolayer, after which cell-cell contact triggers $G_o/G_1$ growth arrest. Terminal differentiation of 3T3-L1 cells to adipocytes depends on proliferation of both pre- and post-confluent preadipocytes. Subsequent stimulation with 3-isobutyl-1-methylxanthane, dexamethasone, and high does of insulin (MDI) for two days prompts these cells to undergo post-confluent mitotic clonal expansion, exit the cell cycle, and begin to express adipocyte-specific genes. Approximately five days after induction of differentiation, more than 90% of the cells display the characteristic lipid-filled adipocyte phenotype. Assessing triglyceride synthesis of 3T3-L1 cells provides a validated model of the insulin-sensitizing ability of the test agent.

It appears paradoxical that an agent that promotes lipid uptake in fat cells should improve insulin sensitivity. Several hypotheses have been proposed in an attempt to explain this contradiction. One premise that has continued to gain research support is the concept of "fatty acid steal" or the incorporation of fatty acids into the adipocyte from the plasma causing a relative depletion of fatty acids in the muscle with a concomitant improvement of glucose uptake [Martin, G., K. Schoonjans, et al. PPARgamma activators improve glucose homeostasis by stimulating fatty acid uptake in the adipocytes. Atherosclerosis 137 Suppl: S75-80, (1998)]. Thiazolidinediones, such as troglitazone and pioglitazone, have been shown to selectively stimulate lipogenic activities in fat cells resulting in greater insulin suppression of lipolysis or release of fatty acids into the plasma [Yamauchi, T., J. Kamon, et al. The mechanisms by which both heterozygous peroxisome proliferator-activated receptor gamma (PPARgamma) deficiency and PPARgamma agonist improve insulin resistance. J Biol Chem 276(44): 41245-54, (2001); Oakes, N. D., P. G. Thalen, et al. Thiazolidinediones increase plasma-adipose tissue FFA exchange capacity and enhance insulin-mediated control of systemic FFA availability. Diabetes 50(5): 1158-65, (2001)]. This action would leave less free fatty acids available for other tissues [Yang, W. S., W. J. Lee, et al. Weight reduction increases plasma levels of an adipose-derived anti-inflammatory protein, adiponectin. J Clin Endocrinol Metab 86(8): 3815-9, (2001)]. Thus, insulin-desensitizing effects of free fatty acids in muscle and liver would be reduced as a consequence of thiazolidinedione treatment. These in vitro results have been confirmed clinically [Boden, G. Role of fatty acids in the pathogenesis of insulin resistance and NIDDM. Diabetes 46(1): 3-10, (1997); Stumvoll, M. and H. U. Haring Glitazones: clinical effects and molecular mechanisms. Ann Med 34(3): 217-24, (2002)].

Chemicals—Penicillin, streptomycin, Dulbecco's modified Eagle's medium (DMEM) was from Mediatech (Herndon, Va.) and 10% FBS-HI (fetal bovine serum-heat inactivated) from Mediatech and Hyclone (Logan, Utah). Methylisobutylxanthine, dexamethasone, indomethacin, Oil red O insulin and all other standard reagents, unless otherwise indicated were bought from Sigma (St. Louis, Mo.).

Test Materials—Troglitazone was purchased from Cayman Chemicals (Ann Arbor, Mich.). Lipoic acid, N-acetylcysteine (NAC), the omega-3 eicosapentaenoic acid (EPA) and the omega-6 gamma linolenic acid (GLA) were from Sigma. Powdered CLA as Clarinol™ CLA was obtained from Lipid Nutrition (Wormerveer, The Netherlands), chromium carnosine (chromium L-β-alanyl-L-histidine) as Carno-Chrome was purchased from FutureCeuticals (Santa Rosa, Calif.) and chromium carnitine was obtained from Albion (Clearfield, Utah). The CLA, NAC and chromium carnosine were formulated with excipient ingredients as described in Table 1 resulting in a formulation termed BION493 containing respectively, 50.2, 4.2 and 0.0017 percent CLA, NAC and chromium carnosine. An isocaloric powder formulation consisting of safflower oil, maltodextran and flavoring was prepared as a placebo control.

Cell culture and Treatment—The murine fibroblast cell line 3T3-L1 was purchased from the American Type Culture Collection (Manassas, Va.) and sub-cultured according to instructions from the supplier. Prior to experiments, cells were cultured in DMEM containing 10% FBS-HI added 50 units penicillin/ml and 50 μg streptomycin/ml, and maintained in log phase prior to experimental setup. Cells were grown in a 5% $CO_2$ humidified incubator at 37° C. Components of the pre-confluent medium included (1) 10% FBS/DMEM containing 4.5 g glucose/L; (2) 50 U/ml penicillin; and (3) 50 μg/ml streptomycin. Growth medium was made by adding 50 ml of heat inactivated FBS and 5 ml of penicillin/streptomycin to 500 ml DMEM. This medium was stored at 4° C. Before use, the medium was warmed to 37° C. in a water bath.

T3-T1 cells were seeded at an initial density of $6\times10^4$ cells/$cm^2$ in 24-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 μM dexamethasone and (4) 10 μg/ml insulin (MDI medium). After three days, the medium was changed to post-differentiation medium consisting of 10 μg/ml insulin in 10% FBS/DMEM.

TABLE 1

BION493 formulation containing chromium carnosine, conjugated linoleic acid, and N-acetylcysteine.

Supplement Facts
Serving Size: 1 pouch (20 g)

| | Amount Per Serving | % Daily Value |
|---|---|---|
| Calories | 102 | |
| Total carbohydrate | 6 g | 2%* |
| Sugars | 0 g | † |
| Chromium (as chromium carnosine) | 200 mcg | 166% |
| Conjugated Linoleic Acid | 6 g | † |
| N-Acetylcysteine | 500 mg | † |

† Daily value not established.
Percent values are based on 2,000-calorie diet.
Other ingredients include natural flavors, malic acid, beet juice powder, citric acid, and silica. Directions for use are to mix one serving with eight ounces of cold water. Keep out of reach of children, store at 15-30° C. (59-86° F.), protect from heat, light and moisture, and not to purchase if the seal is broken.

BION493 was dissolved in dimethyl sulfoxide (DMSO) and added to the culture medium to achieve a concentration of 50 μg/mL at Day 0 of differentiation and throughout the maturation phase (Days 6 or 7). CLA was also dissolved in DMSO and added to the culture medium to obtain final concentrations of 50, 10, 5 and 1 μg/mL. The other conjugated fatty acids, EPA and GLA were dosed at 50 μg/mL. NAC and lipoic acid were tested at 25 and 5 μg/mL, respectively. The two concentrations of chromium as chromium carnitine were 0.005 and 0.04 μg/mL. A DMSO solvent control was run concurrently with each experiment.

Figure 4:
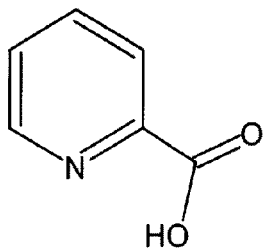
FIG. 4 illustrates several different chromium-specific ligands.
Figure 4:
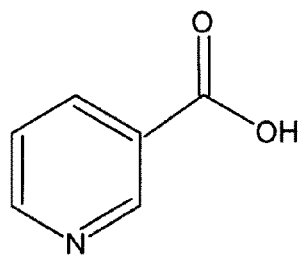
Figure 4:
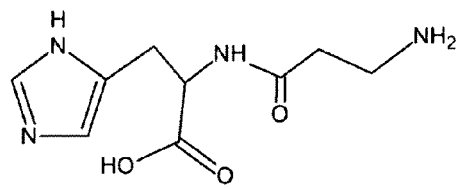
Figure 5:
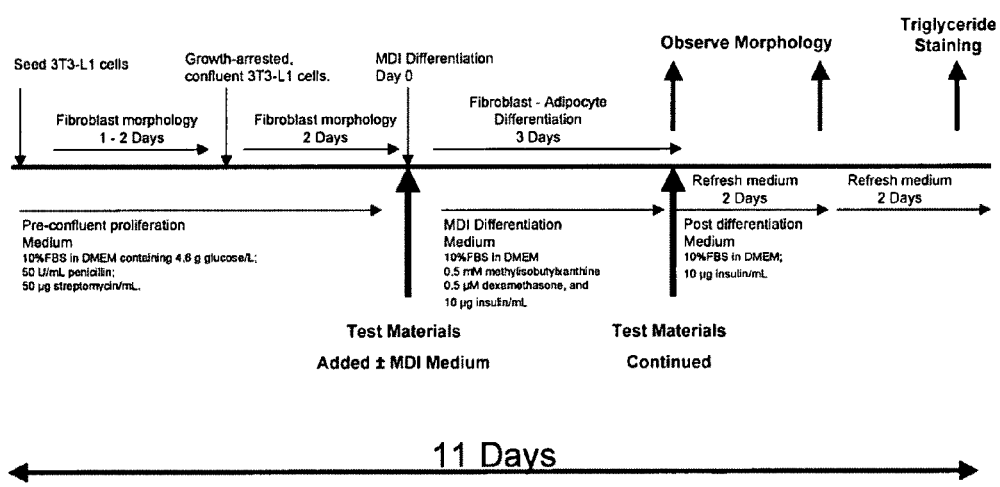
FIG. 5 is a schematic of a representative testing procedure for assessing lipogenic effects of a test material on developing and maturing adipocytes. The 3T3-L1 murine fibroblast model was used to study the potential effects of the test compounds on adipocyte adipogenesis.

Whenever fresh media were added, fresh test material was also added. DMSO was chosen for its polarity and the fact that it is miscible with the aqueous cell culture media. As a positive control troglitazone, was added to achieve final concentrations of 4.4 μg/mL (10 μM). Differentiated, D6/D7 3T3-L1 cells were stained with 0.36% Oil Red O. The complete procedure for differentiation and treatment of cells with test materials is outlined schematically in FIG. 4.

Oil Red O Staining—Triglyceride content of D6/D7-differentiated 3T3-L1 cells was estimated with Oil Red O according to the method of Kasturi and Joshi [Kasturi, R. and Joshi, V. C. Hormonal regulation of stearoyl coenzyme A desaturase activity and lipogenesis during adipose conversion of 3T3-L1 cells. J Biol Chem, 257: 12224-12230, 1982]. Monolayer cells were washed with PBS (phosphate buffered saline, Mediatech) and fixed with 10% formaldehyde for ten minutes. Fixed cells were stained with an Oil Red O working solution of three parts 0.6% Oil Red O/isopropanol stock solution and two parts water for one hour and the excess stain was washed once with water. The resulting stained oil droplets were extracted from the cells with isopropanol and quantified by spectrophotometric analysis at 540 nm (MEL312e BIO-KINETICS READER, Bio-Tek Instruments, Winooski, Vt.). Results for test materials and the positive controls indomethacin and troglitazone were represented relative to the 540 nm absorbance of the solvent controls.

Statistical Calculations and Interpretation—Solvent and troglitazone controls as well as all test materials were replicated in duplicate. A Lipogenic Index (LI) was computed as the nonpolar lipid incorporation in test 3T3-L1 adipocytes relative to the nonpolar lipid accumulation of adipocytes in the solvent controls. A positive response was defined as an increase in lipid accumulation assessed by Oil Red O staining greater than the respective upper 95% confidence interval of the solvent control computed from the error mean square determined by analysis of variance (two-tail, Excel; Microsoft, Redmond, Wash.).

Synergy calculations—Estimates of the expected synergistic lipogenic effect of various conjugated fatty acid, thiol or chromium combinations were made using the relationship: $1/[LI]c = X/[LI]_A + Y/[LI]_B + Z/[LI]_C$ where LI=the lipogenic index represented as fraction of the lipid incorporation of the solvent controls, X, Y and Z are the relative fractions of each component A, B and C in the test mixture, and X+Y+Z=1. Synergy was inferred if the mean of the estimated LI fell below the 95% confidence interval of the corresponding observed LI. This definition of synergy, involving comparison of the effects of a combination with that of each of its components, has been described by Berenbaum [Berenbaum M C. What is synergy? *Pharmacol Rev*. June 1989; 41 (2): 93-141.

Figure 7:
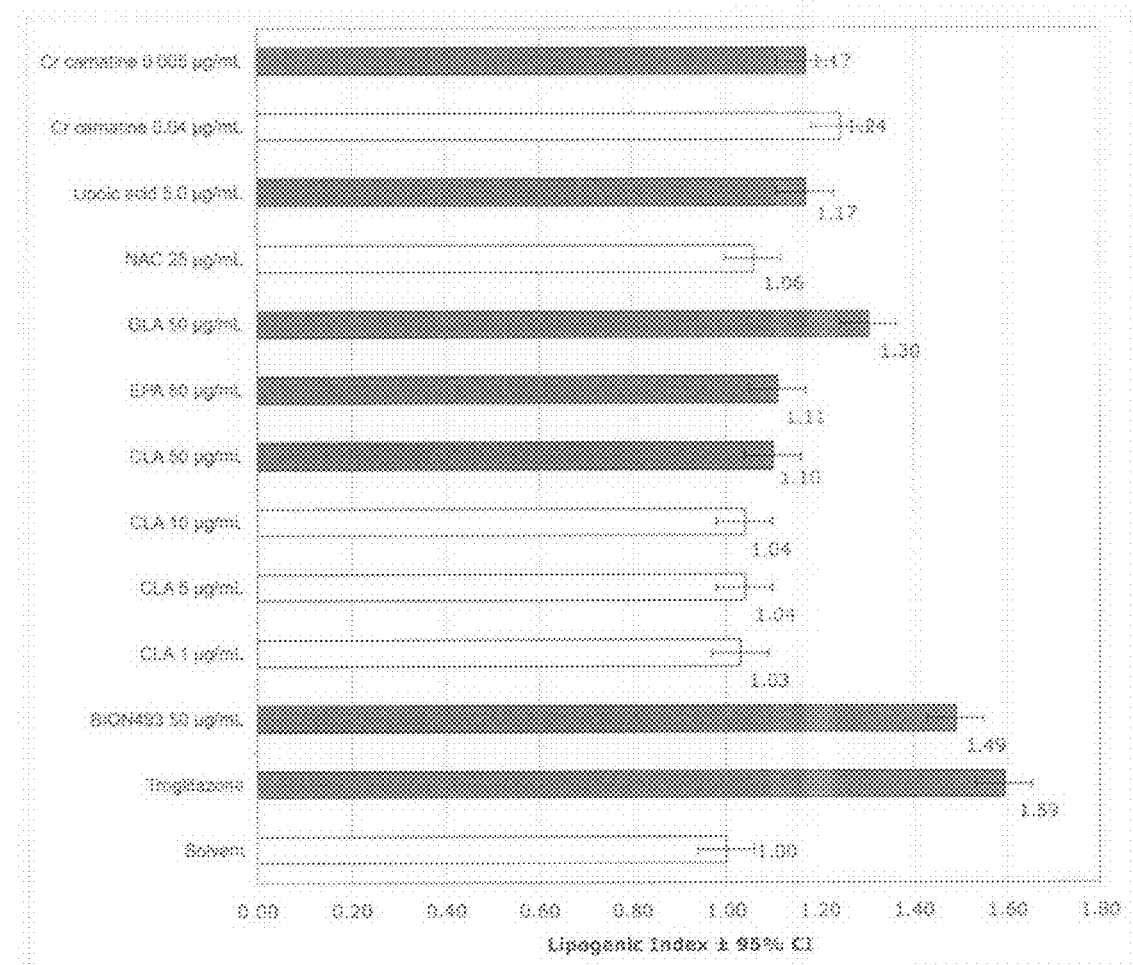
FIG. 7 is a graphic representation depicting the relative nonpolar lipid content (Lipogenic Index) of 3T3-L1 adipocytes treated with test materials or the positive control troglitazone relative to the solvent control. Dark bars are significantly different (p<0.05) from the solvent control; error bars represent the 95% confidence limits.

Results—The positive control troglitazone increased lipogenesis 59 percent relative to the solvent controls (FIG. 7). With an increase in lipid incorporation of 49 percent, the BION493 formulation was the most potent of the test materials. GLA was the most potent of the conjugated fatty acids increasing LI by 30 percent, with EPA and CLA producing an increase in LI of approximately 10 percent. Below 50 μg/mL, CLA did not increase the LI. Both concentrations of chromium as chromium carnitine increased lipid incorporation in a dose-dependent manner, 24 percent at 0.04 μg/mL and 17 percent at 0.005 μg/mL.

Figure 8:
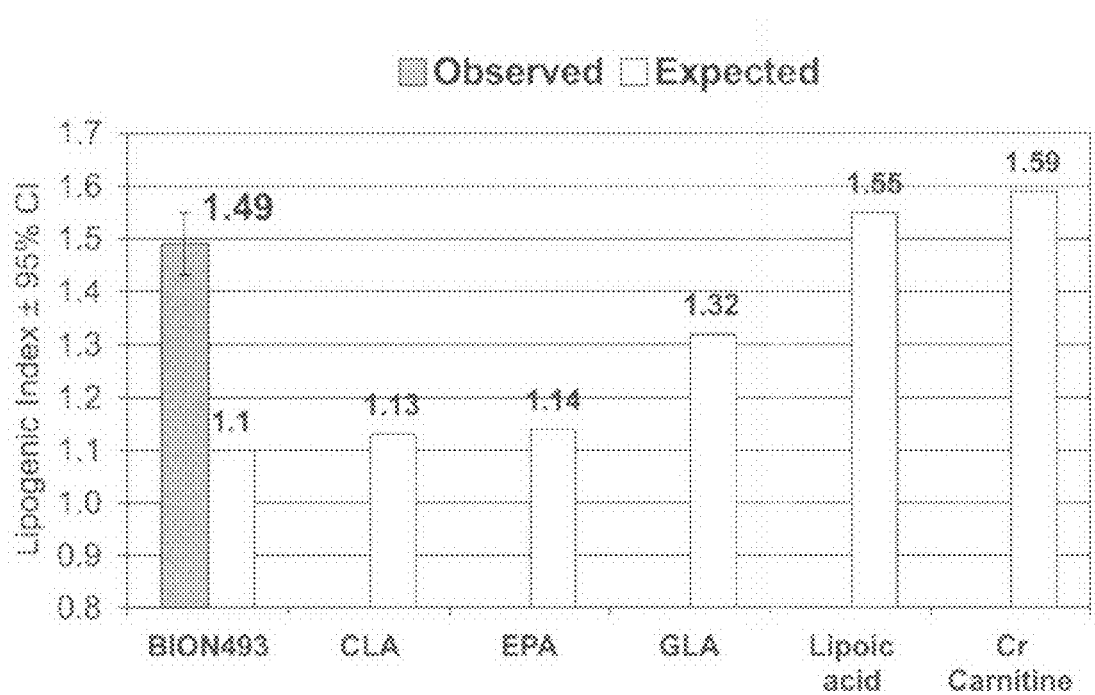
FIG. 8 depicts the observed and expected LI for BION493 with the expected value computed from the singular responses of the three individual components. Expected responses estimated by mathematically substituting only CLA, GLA, EPA, lipoic acid or chromium carnitine LI with the NAC/chromium carnosine combination are also presented. Mean Lipogenic Indexes below the lower 95% Confidence Interval indicate synergy of the BION493 formulation.

FIG. 8 depicts the observed and expected LI for BION493 with the expected value computed from the singular responses of the three individual components. Expected responses estimated by mathematically substituting only CLA, GLA, EPA, lipoic acid or chromium carnitine LI with the NAC/chromium carnosine combination are also presented. From these calculations, it appears that NAC and chromium synergistically interact with CLA to increase free fatty acid uptake by adipocytes. Similarly, the calculations predict that NAC and chromium carnosine would synergistically interact with other conjugated fatty acids such as EPA and GLA. On the other hand, lipoic acid and chromium carnitine may substitute for NAC and chromium carnosine to produce similar synergy with CLA.

The increased triglyceride incorporation seen in the 3T3-L1 adipocyte model is an indication of the potential of BION493 to increase insulin sensitivity. Physiologically, when the adipocyte pulls free fatty acids from the plasma, a concomitant loss of fat is seen in associated muscle tissue. This loss of fat in the muscle tissue results in increased sensitivity to insulin by the muscle.

Example 2

Increased Adiponectin Secretion in the TNFα/3T3-L1 Adipocyte Model by BION493 and Components The Model—The 3T3-L1 murine fibroblast model as described in Example 1 was used in these experiments.

Figure 9:
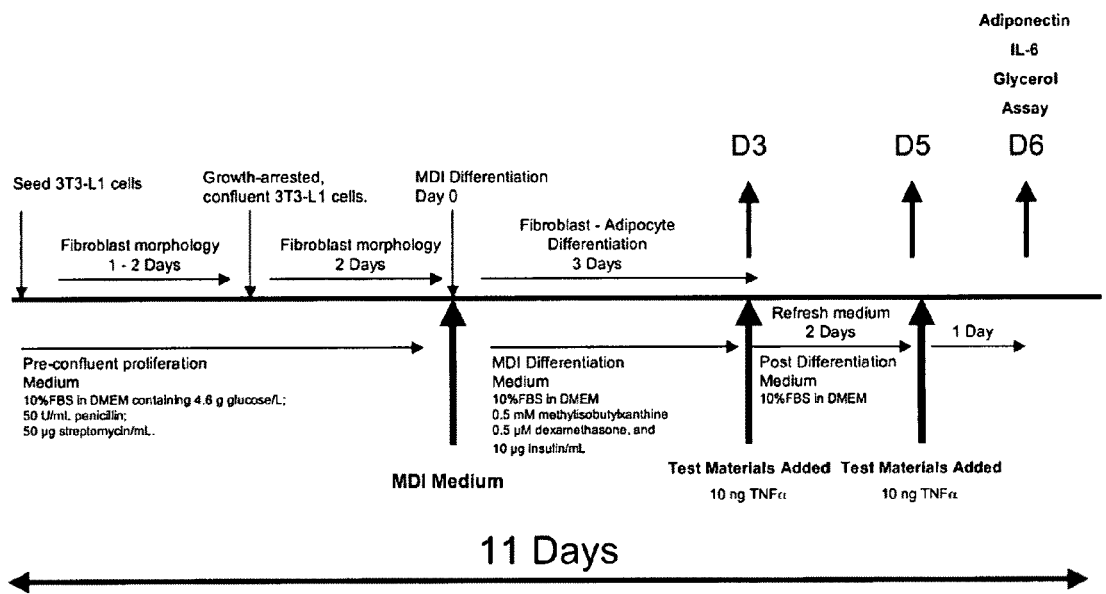
FIG. 9 is a schematic of the representative testing procedure for assessing effects of test materials on lipolysis and secretion of IL-6 and adiponectin using the TNFα-stimulated 3T3-L1 adipocyte model.

Cell Culture and Treatment—Cell culture procedures and standard chemicals, and statistical procedures used were as noted in Example 1. BION 493 as described in Example 1 was used as the test material and dosed at 100, 50, 25 and 12.5 μg BION493/mL. This corresponded to 21.4, 10.7 and 5.4 μg CLA/mL, 3.8, 1.9 and 1.0 μg NAC/mL and 0.0007, 0.0004 and 0.0002 μg $Cr^{+++}$/mL.. Concentrations for the positive control pioglitazone were 2.5, 1.25 and 0.625 μg/mL. The processes of cell culture and treatment for assessing effect of the test materials on adiponectin secretion in the presence of TNFα are presented schematically in FIG. 9. Test materials were added four hours prior to the addition of TNFα at a concentration of 10 ng/mL. Following overnight incubation, the supernatant media was sampled for determination of adiponectin.

Adiponectin assay—The adiponectin secreted into the medium was quantified using the Mouse Adiponectin Quantikine® Immunoassay kit with no modifications (R&D Systems, Minneapolis, Minn.). Information supplied by the manufacturer indicated that recovery of adiponectin spiked in mouse cell culture media averaged 103% and the minimum detectable adiponectin concentration ranged from 0.001 to 0.007 ng/ml.

Statistical Calculations and Interpretation—Test materials and were assayed in duplicate, while solvent and troglitazone controls were replicated eight times. Adiponectin secretion was represented relative to the adiponectin secretion of the TNFα only controls as the adiponectin index (Adiponectin) $_{Test}$/[Adiponectin]$_{TNFα\ control}$) and differences among the means were analyzed by the student's t-test assuming a five percent probability of a type I error (Excel; Microsoft, Redmond, Wash.).

Figure 10:
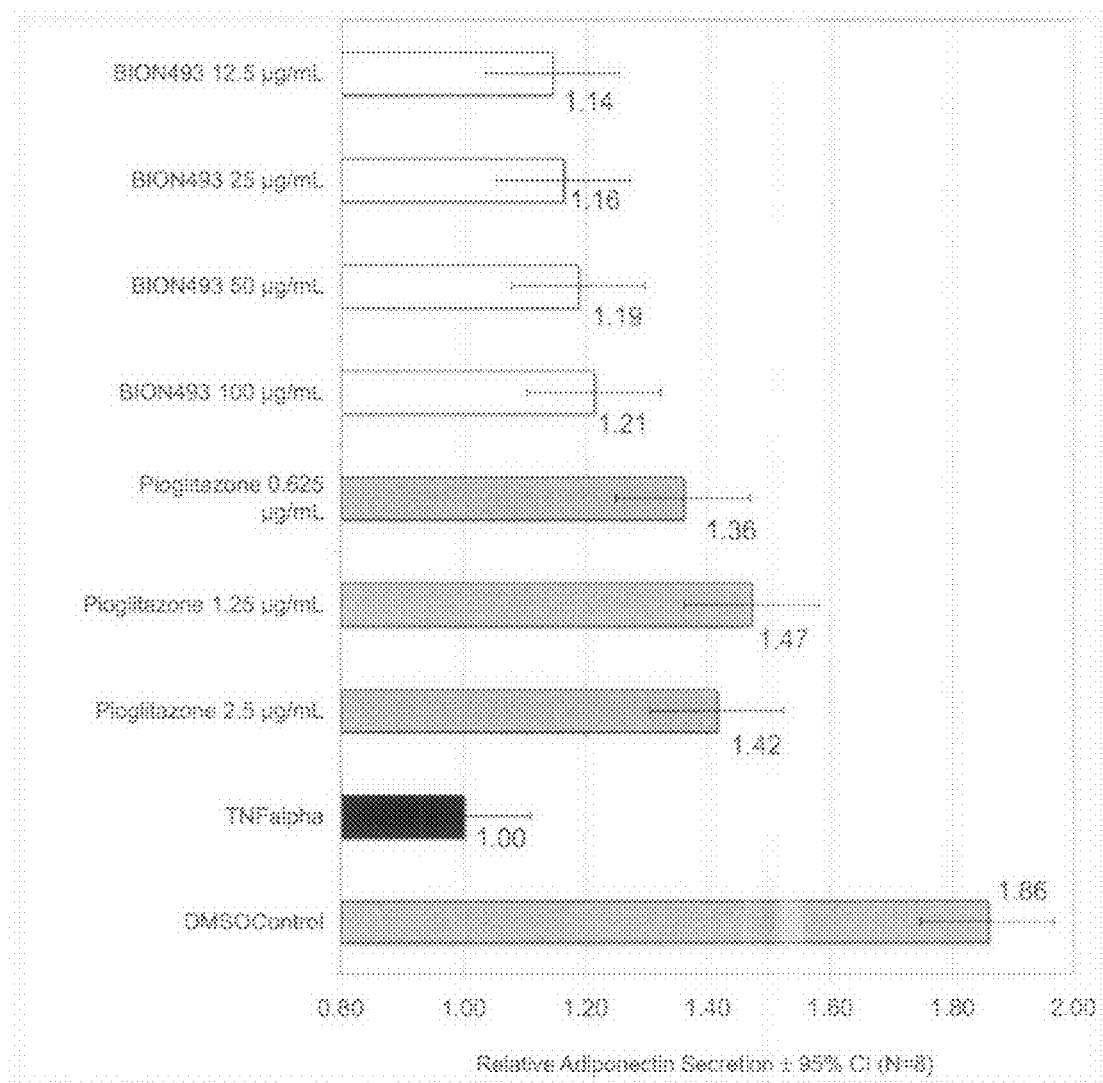
FIG. 10 is a bar graph depicting the dose-related increase in adiponectin secretion by BION493 and pioglitazone in mature 3T3-L1 adipocytes stimulated overnight with TNFα. Error bars are 95% Confidence Intervals.
Figure 11:
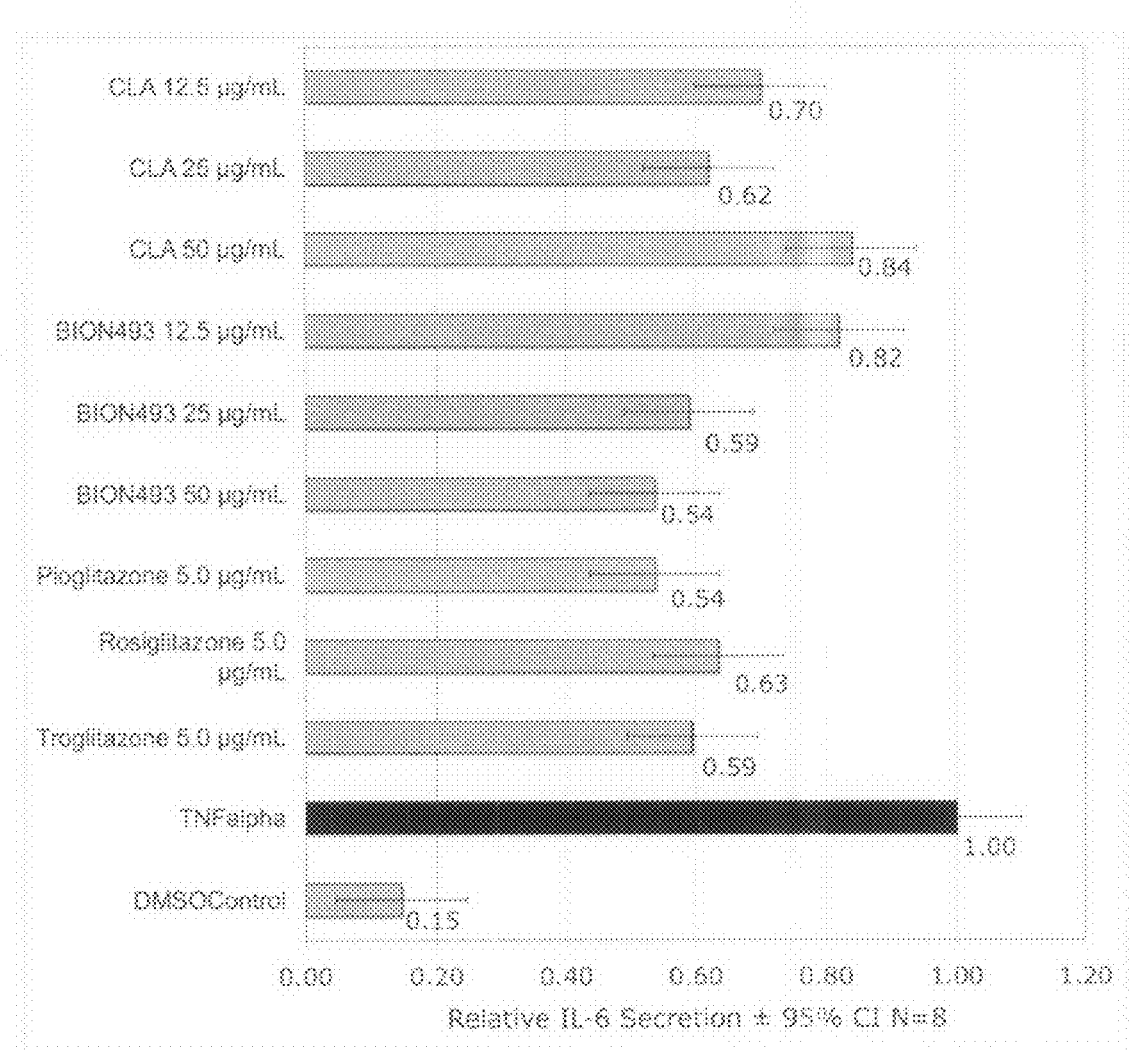
FIG. 11 is a bar graph illustrating the dose-related inhibition of IL-6 secretion in TNFα-stimulated, mature 3T3-L1 adipocytes by BION493 and CLA contrasted with pioglitazone, rosiglitazone and troglitazone. Error bars are 95% Confidence Intervals.
Figure 12:
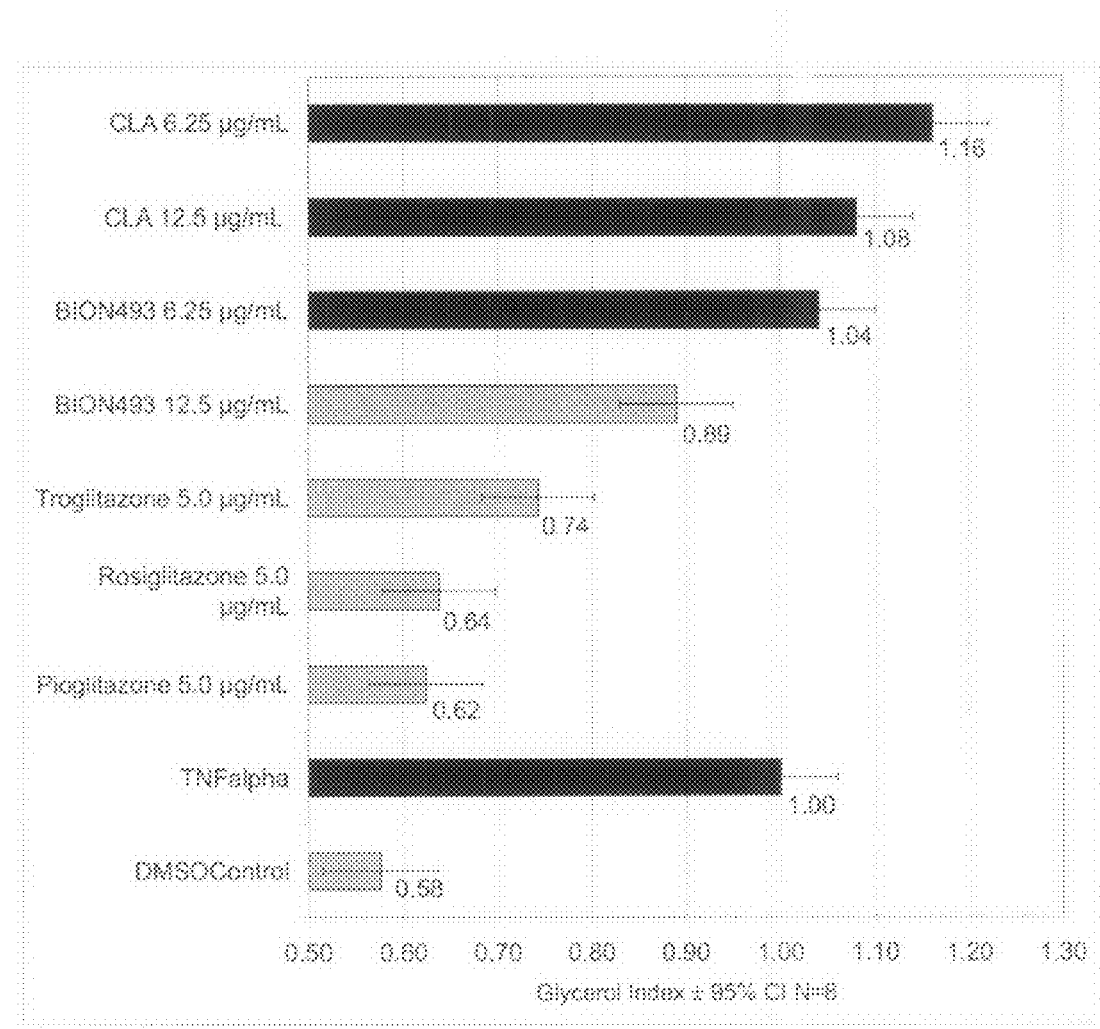
FIG. 12 is a bar graph illustrating the novel observation that BION493 inhibits lipolysis in TNFα-stimulated 3T3-L1 adipocytes, while CLA stimulates lipolysis. Error bars are 95% Confidence Intervals.

Results—TNFα decreased adiponectin secretion nearly 50% relative to the DMSO control (FIG. 10). All doses of pioglitazone increased adiponectin secretion in the presence of TNFα to a similar extent averaging 42%. Similarly, all doses of BION493 increased adiponectin secretion averaging 18% overall.

The ability of BION493 to increase adipocyte adiponectin secretion in the presence of supraphysiological concentrations of TNFα supports the usefulness of this formulation for the prevention or treatment of inflammatory conditions involving suboptimal adipocyte functioning.

Example 3

Decreased IL-6 Secretion in the TNFα/3T3-L1 Adipocyte Model by a CLA Formulation and Components The Model—The 3T3-L1 murine fibroblast model as described in Example 1 was used in these experiments.

Cell Culture and Treatment—Cell culture procedures and standard chemicals, and statistical procedures used were as noted in Example 1. BION 493 as described in Example 1 was used as the test material and dosed at 100, 50, 25 and 12.5 μg BION493/mL. This corresponded to 21.4, 10.7 and 5.4 μg CLA/mL, 3.8, 1.9 and 1.0 μg NAC/mL and 0.0007, 0.0004 and 0.0002 μg $Cr^{+++}$/mL. CLA as described in Example 1 was dosed at 50, 25 and 12.5 μg/mL. All positive controls troglitazone, rosiglitazone and pioglitazone were tested at 5.0 μg/mL. The processes of cell culture and treatment for assessing effect of the test materials on IL-6 secretion in the presence of TNFα are presented schematically in FIG. 9. Test materials were added four hours prior to the addition of TNFα at a concentration of 10 ng/mL. Following overnight incubation, the supernatant media was sampled for determination of IL-6.

Interleukin-6 assay—The IL-6 secreted into the medium in response to TNFα stimulation was quantified using the Quantikine® Mouse IL-6 Immunoassay kit with no modifications (R&D Systems, Minneapolis, Minn.). Information supplied by the manufacturer indicated that recovery of IL-6 spiked in mouse cell culture media averaged 99% with a 1:2 dilution and the minimum detectable IL-6 concentration ranged from 1.3 to 1.8 μg/mL. All supernatant media samples were diluted 1:30 for quantification.

Statistical Calculations and Interpretation—Test materials and were assayed in duplicate, while solvent and troglitazone controls were replicated eight times. IL-6 secretion was represented relative to the IL-6 secretion of the TNFα only controls as the IL-6 index and differences among the means were analyzed by the student's t-test assuming a five percent probability of a type I error (Excel; Microsoft, Redmond, Wash.).

Results—Treatment with 10 ng TNFα/mL induced a 6.7-fold increase in IL-6 secretion relative to controls. The positive controls, as well as all doses of BION493 and CLA inhibited IL-6 secretion in TNFα-stimulated adipocytes indicating the ability to reduce secretion of additional pro-inflammatory cytokines in response to a pro-inflammatory stimulus. Over all three doses, BION493 was more inhibitory than CLA alone, 35% vs 28%, respectively. The attenuation of IL-6 secretion as demonstrated in this example indicates potential of the test materials to increase insulin sensitivity in obesity, metabolic syndrome, NIDDM or other inflammatory metabolic states.

Example 4

Decreased Lipolysis in the TNFα/3T3-L1 Adipocyte Model by a CLA Formulation and Components The Model—The 3T3-L1 murine fibroblast model as described in Example 1 was used in these experiments.

Cell Culture and Treatment—Cell culture procedures and standard chemicals, and statistical procedures used were as noted in Example 1. BION 493 as described in Example 1 was used as the test material and dosed at 12.5 and 6.25 μg BION493/mL. This corresponded to 5.4 and 2.7 μg CLA/mL, 1.0 and 0.5 μg NAC/mL and 0.0002 and 0.001 μg $Cr^{+++}$/mL. CLA as described in Example 1 was dosed at 12.5 and 6.25 μg/mL. All positive controls troglitazone, rosiglitazone and pioglitazone were tested at 5.0 μg/mL. The processes of cell culture and treatment for assessing effect of the test materials on glycerol secretion in the presence of TNFα are presented schematically in FIG. 9. Test materials were added four hours prior to the addition of TNFα at a concentration of 10 ng/mL. Following overnight incubation, the supernatant media was sampled for determination of glycerol as a measure of free fatty acid release (lipolysis).

Glycerol assay—TNFα induced free fatty acid release from 3T3-L1 adipocytes was quantified by measuring glycerol secretion into the medium. Glycerol was measured spectrophotometrically using the Free Glycerol Determination Kit (F6428, Sigma) and an EL 312e Microplate BIO-KINET-ICS spectrophotometer (BioTek, Winooski, Vt.). In this assay, glycerol is phosphorylated by glycerol kinase and ATP to form glycerol-1-phosphate (G-1-P) and ADP. G-1-P is then oxidized by glycerol phosphate oxidase (GPO) to dihydroxyacetone phosphate (DAP) and hydrogen peroxide ($H_2O_2$). Peroxidase (POD) catalyzes the coupling of H2O2 with 4-aminoantipyrine (4-AAP) and sodium N-ethyl-N-(3-sulfopropyl)m-anisidine (ESPA) to produce a quinoneimine dye that shows an absorbance maximum at 540 nm. This increase in absorbance at 540 nm is directly proportional to the free glycerol concentration of the sample. Control, non-stimulated D6/D7 3T3-L1 adipocytes produced, on average, 772 ng glycerol/mL. Treatment with 10 ng TNFα/mL induced a 2.9-fold increase in glycerol secretion relative to controls.

Statistical Calculations and Interpretation—Test materials and were assayed in duplicate, while solvent and positive controls were replicated eight times. Glycerol secretion was represented relative to the glycerol secretion of the TNFα only controls as the Glycerol Index and differences among the means were analyzed by the student's t-test assuming a five percent probability of a type I error (Excel; Microsoft, Redmond, Wash.).

Results—TNFα induce a 1.7-fold increase in glycerol release relative to the solvent control, while pioglitazone, rosiglitazone and troglitazone inhibited glycerol release, respectively, 38, 36 and 26% relative to the TNFα only treatment. BION493 inhibited lipolysis only at the 12.5 μg/mL, which contained 5.4 μg CLA/mL, 1.0 μg NAC/mL and 0.0003 μg Cr+++/mL. Conversely, CLA increased glycerol release relative to TNFα only. This result demonstrates the potential for CLA to decrease insulin sensitivity and an attenuation of this effect with the addition of NAC and chromium.

Example 5

BION493 Overcomes the Depression of Adiponectin Secretion by Saquinavir in TNFα-Stimulated 3T3-L1 Adipocytes The Model—The 3T3-L1 murine fibroblast model as described in Example 1 was used in these experiments.

Cell Culture and Treatment—Cell culture procedures and standard chemicals, and statistical procedures used were as noted in Example 1. BION 493 as described in Example 1 was used as the test material and dosed at 12.5 μg BION493/mL. This corresponded to 5.4 μg CLA/mL, 1.0 μg NAC/mL and 0.0002 μg $Cr^{+++}$/mL. The concentration for the positive control pioglitazone was 5.0 μg/mL. Commercial capsules of saquinavir (Invirase, Roche Pharmaceuticals) were used and concentrations of active protease inhibitor to which the 3T3-L1 adipocytes were exposed were 5.0, 2.5, and 1.25 μg/mL. A 1:10 combination of saquinavir and BION493 was formulated to deliver concentrations of 1.25 and 12.5 μg/mL, respectively, of each material. The processes of cell culture and treatment for assessing effects of the test materials on adiponectin secretion in the presence of TNFα are presented schematically in FIG. 9. Test materials were added four hours prior to the addition of TNFα at a concentration of 10 ng/mL. Following overnight incubation, the supernatant media was sampled for determination of adiponectin.

Adiponectin assay—The adiponectin secreted into the medium was quantified using the Mouse Adiponectin Quantikine® Immunoassay kit with no modifications (R&D Systems, Minneapolis, Minn.). Information supplied by the manufacturer indicated that recovery of adiponectin spiked in mouse cell culture media averaged 103% and the minimum detectable adiponectin concentration ranged from 0.001 to 0.007 ng/ml.

Statistical Calculations and Interpretation—Test materials and were assayed in duplicate, while solvent and troglitazone controls were replicated eight times. Adiponectin secretion was represented relative to the adiponectin secretion of the TNFα only controls as the adiponectin index (Adiponectin)$_{Test}$/[Adiponectin]$_{TNFα\ control}$) and differences among the means were analyzed by the student's t-test assuming a five percent probability of a type I error (Excel; Microsoft, Redmond, Wash.).

Figure 13:
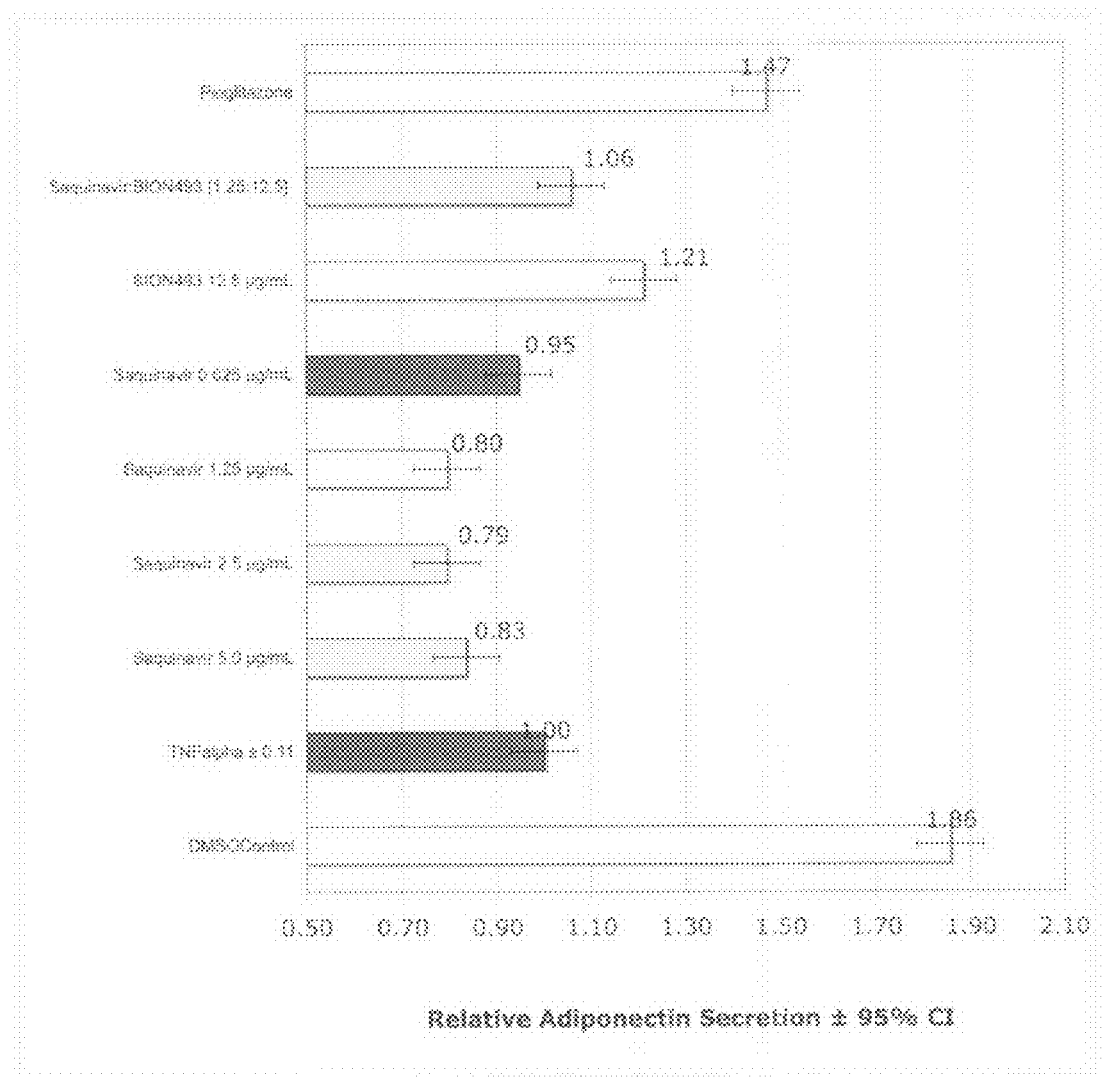
FIG. 13 is a bar graph depicting the inhibition of adiponectin secretion by the anti-retroviral, protease inhibitor saquinavir in TNFα-stimulated 3T3-L1 adipocytes and the rescue of this inhibition by BION493. Error bars are 95% Confidence Intervals.

Results—TNFα decreased adiponectin secretion nearly 50% relative to the DMSO control (FIG. 13). Pioglitazone increased adiponectin secretion in the presence of TNFα by 42%, while the 12.5 µg BION493/mL concentration increased adiponectin secretion 21% above the TNFα control. Conversely, sequinavir decreased adiponectin secretion relative to the TNFα control by 17% at 5.0 µg/mL, 21% at 2.5 µg/mL, and 20% at 1.25 µg/mL. All of these decreases in adiponectin secretion were below that of the TNFα control. The 1:10 combination of saquinavir/BION493 overcame the depression of adiponectin secretion by saquinavir alone, but did not increase adiponectin above the TNFα control.

This example demonstrates the unique and unexpected ability of BION493 to increase adipocyte adiponectin secretion in the presence of saquinavir, thus demonstrating usefulness in the treatment and prevention of protease-mediated depression of adiponectin secretion and in inflammatory conditions involving suboptimal adipocyte functioning.

Example 6

Clinical Trial to Assess the Tolerability Safety and Efficacy of a Dietary Formulation Containing Conjugated Linoleic Acid, N-Acetylcysteine and Chromium Carnosine for the Management of Antiretroviral Therapy (ART)-Associated Fat Maldistribution and Dyslipidemia in HIV-Positive Men Study design—This double-blinded, placebo controlled study was designed to evaluate the tolerability and provide limited safety and efficacy data of a CLA formulation for management of ART-associated hyperlipidemia in HIV-positive persons. Over a 12-week or 15-week period, 17 subjects (i) with a history of normal serum lipids prior to receiving ART and (ii) elevated serum lipids while receiving ART were randomly assigned to receive the CLA formulation powder or an isocaloric placebo powder to be mixed with fluid and taken daily. Participants were seen in the clinic at baseline, at six weeks and at 12 weeks for evaluation. A subset of six subjects (three per group) who had discontinued their lipid-lowering drugs for the first 12 weeks of the study resumed their discontinued medication after 12 weeks while remaining on the CLA formulation or the isocaloric placebo regimen for an additional three weeks. At the 15-week clinic visit for this subset, only serum lipid variables were assessed.

Study clinic location—This study was conducted at a single clinic site in New York, N.Y. during the period of May 2003 through Sep. 2004.

Test material—The test powder formulation consisted of CLA, NAC, and chromium as chromium carnosinate (Carno-Chrom, FutureCeuticals, Santa Rosa, Calif.). As a once daily supplement, the formulation delivered six g CLA, 500 mg NAC, and 200 µg chromium (Table 1). For this study, a fruit-flavored powder containing the active ingredients were mixed with water and taken daily for 12 or 15 weeks. The placebo group received an isocaloric powder formulation consisting of safflower oil, maltodextran and flavoring. Both the CLA formulation and the placebo were manufactured by Garden State Nutritionals (West Caldwell, N.J.).

Subjects—Subjects for this study were selected from HIV/AIDS patients exhibiting increased fasting serum cholesterol, LDL-cholesterol, or triglycerides coincident with antiretroviral therapy with or without altered blood glucose. Participants were required to report to the clinic for three visits following an overnight fast. At each of the three visits, a physical exam was conducted that included drawing of two blood samples for serum lipids, complete blood counts, serum chemistries and plasma insulin. A subset of six patients that discontinued lipid-lowering drugs prior to entering the study elected an additional clinic visit at 15 weeks to assess the effect of the CLA formulation or placebo in combination with their discontinued medications. At this fourth clinical visit, only a serum lipid panel was performed.

The clinical protocol was reviewed by an external, independent review board and found satisfactory. All subjects executed informed consent forms. Subjects received compensation for participation in the study. The subset of patients selecting the additional three-week follow-up with concurrent lipid-lowering medications was given additional compensation.

Inclusion criteria—Primary study variables included fasting serum levels of LDL-cholesterol greater than 130 mg/dL or total cholesterol greater than 200 mg/dL; or fasting serum triglycerides greater than 200 mg/dL; with or without fasting blood glucose between 110 and 130 mg/100 mL. Additional inclusion criteria were baseline laboratory values measured within two weeks prior to initiating study as follows: (1) serum creatinine <1.5-times the upper limit of normal, (2) liver enzymes ALT and AST <5-times the upper limit of normal, and (3) total serum bilirubin <1.5-times the upper limit of normal.

Exclusion criteria (any one) included: (1) unstable viral load (greater than two log unit change from last visit) with antiretroviral therapy; (2) under 18 years of age; (3) currently taking, or have taken in the past 60 days, any prescription cholesterol, triglyceride-lowering, anabolic, weight loss or blood glucose/diabetes medications; (4) currently taking dietary supplements that are advertised to reduce serum cholesterol, increase muscles mass, promote weight loss, address blood glucose/insulin sensitivity or have anabolic activity; (5) currently receiving treatment for or having been treated for any cancers; (6) a history of hypoglycemia; (7) type 2 diabetes; (8) serum markers for liver function (ALT or AST) greater than five times normal values within the last six months; (9) active alcohol or substance abuse sufficient, in the investigator's opinion, to prevent adequate compliance with the study test materials or to increase the risk of developing pancreatitis or chemical hepatitis; (10) liposuction or other cosmetic surgery to alter body fat distribution; (11) intractable diarrhea (=6 loose stools per day for at least seven consecutive days within 30 days prior to baseline; (12) vomiting lasting more than four days within one month prior to study initiation; (13) life expectancy less than 12 months; or (14) any other clinical conditions or prior therapy that, in the opinion of the clinical investigator, would make the patient unsuitable for study, or unable to comply with the dosing regimen.

Evaluations—At initiation, estimates of nutrient intake were made using a daily dietary recall form covering a period of three to seven days. All other evaluations were performed at baseline, six and twelve weeks. An additional fasting serum lipid panel was run at 15 weeks that included six subjects returning to their lipid lowering medications while remaining on their study formulation. The serum lipid panel included total cholesterol, HDL cholesterol, LDL cholesterol (calculated) and triglycerides. Serum metabolic variables included fasting glucose, fasting insulin, alkaline phosphatase, urea nitrogen, sodium, total protein, potassium, creatinine, chloride, calcium, total bilirubin, carbon dioxide, alanine aminotransferase (ALT) and aspartate aminotransferase (AST). Complete blood counts were performed including total and differential leukocytes including platelets, HIV-1, RNA PCR $2^{nd}$ generation with limit of detection <50 copies and CD4 counts.

Serious adverse event reporting—Assessment of compliance and request for adverse reactions was made at clinic visits two and three. Compliance was excellent in both the CLA formulation group as well as the placebo group. One subject in each treatment arm reported comments on taste or mixability. For the purposes of this study, a serious adverse event was defined as any event that was fatal, life threatening, that is, the subject was, in the view of the investigator, at immediate risk of death as the event occurred, was disabling or incapacitating or required inpatient hospitalization. No serious adverse events occurred during this study.

Statistical analysis—Continuous variables were analyzed using analysis of variance procedures. The log transformation was used for all variables although the effect of compressing the distribution had little effect on the interpretation or power of the statistical analysis. The paired t-test was used to analyze differences within the groups from baseline to 6 weeks and from baseline to 12 weeks. The mean differences between groups at baseline, 6 weeks and 12 weeks were assessed with an unpaired t-test and with 95% confidence intervals calculated according to standard procedures. Medians were analyzed by the nonparametric Wilcoxin signed rank test. All tests were two-tailed and the probability of rejecting the Null hypothesis when true was set at the nominal 5% level. Statistical calculations were performed using Excell (Microsoft, Redmond, Wash.) and Data Desk software package (Data Desk, Ithaca, N.Y.). The nonparametric Wilcoxin signed rank test for differences between medians provided the greatest power for detecting differences. Therefore, all tables and figures were constructed using the median values with parenthetic minimum and maximum values to provide an estimate of variability.

Insulin sensitivity was calculated in the fasting state. The quantitative insulin sensitivity check index (QUICKI0 was used and calculated as the inverse of the sum of the logarithmic transformation of fasting concentrations of serum insulin and plasma glucose. $QUICKI(G_b, I_b) = (1/\log(G_b * I_b) = 1/(\log(G_b) + \log(I_b))$, where Gb (mg/dL) is the fasting glucose concentration and Ib (µU/mL) is the fasting insulin concentration. This index has previously been shown to be a surrogate measure of insulin sensitivity, given the significant correlation with glucose disposal during euglycemic hyperinsulinemic glucose clamp tests.

Results

Subjects—Volunteers for the study were recruited over an 11-month period from May 2003 through Apr. 2004. Overall, 17 subjects were enrolled in the study, eight in the placebo and nine in the test group. Assignment to treatment was made using a predetermined randomization table. Three individuals dropped out of the study in the first six weeks, two from the placebo group and one from the CLA formulation group. One subject (test group) was eliminated for antiretroviral drug failure during the initial washout phase. A description of the placebo and test subjects with regard to age, CDC AIDS classification, year of diagnosis, daily exercise estimate, energy rating, current medications, and medications discontinued for the study is provided in Tables 2A and 2B for the placebo and test subjects, respectively.

TABLE 2A

Description of placebo subjects.

| Placebo Subjects Variable | 001 Pretest† May 1, 2003 | 009 Pretest† Jul. 21, 2003 | 007 Pretest Jun. 5, 2003 | 008 Pretest May 12, 2003 |
|---|---|---|---|---|
| Age [yrs] | 40 | 43 | 39 | 55 |
| CDC AIDS Category | C | | A | B |
| Year of Diagnosis | 1997 | | 1998 | 1994 |
| Years Infected | 7.0 | | 6.0 | 10.0 |
| Exercise | | | | |
| Times/week | 5 | 4 | 3 | 0 |
| Minutes/period | 60 | 60 | 60 | 0 |
| Daily activity [1-5] | Moderate (4) | Moderate (4) | Moderate (4) | Moderate (4) |
| Energy rating [0-4] | Very much (4) | Quite a lot (3) | Very much (4) | Quite a lot (3) |
| Medications - Current | 1. EPIVIR | 1. EPIVIR | 1. CRIXIVAN | 1. EPIVIR |
| | 2. SUSTIVA | 2. VIRACEPT | 2. NORVIR | 2. KALETRA |
| | 3. VIREAD | 3. VIREAD | 3. VIREAD | 3. SUSTIVA |
| | | | 4. ZIAGEN | 4. VIDEX®ECV |
| | | | | 5. VIREAD |
| Medications - Dropped | 1. TRICOR | 1. LIPTOR | 1.LIPITOR | None |
| | 2. Nutrivir NSA | 2. Nutrivir NSA | | |
| Health Rated [1-6] | Very Good (5) | Very Good (5) | Very Good (5) | Very Good (5) |
| Any Illness | Osteoporosis Hepatitis B | No | No | No |
| Cigarettes | No | No | No | No |
| Placebo Subjects Variable | 010 Pretest Jun. 16, 2003 | 014 Pretest Mar. 29, 2004 | 017 Pretest May 17, 2004 | 018 Pretest Mar. 29, 2004 |
| Age [yrs] | 36 | 39 | 40 | 30 |
| CDC AIDS Category | A | A | A | B |
| Year of Diagnosis | 1993 | 1996 | 1991 | 1991 |
| Years Infected | 11.0 | 8.0 | 13.0 | 13.0 |

TABLE 2A-continued

Description of placebo subjects.

Exercise

| | | | | |
|---|---|---|---|---|
| Times/week | 3 | 2 | 3 | 0 |
| Minutes/period | 60 | 60 | 45 | 0 |
| Daily activity [1-5] | Moderate (4) | Moderate (4) | Moderate (4) | Moderate (4) |
| Energy rating [0-4] | Quite a lot (3) | Quite a lot (3) | Quite a lot (3) | Very much (4) |
| Medications - Current | 1. EFFEXOR<br>2. EPIVIR<br>3. FORTOVASE<br>4. NORVIR<br>5. VIREAD<br>6. ZERIT | 1. EPIVIR<br>2. FORTOVASE<br>3. NORVIR<br>4. VIDEX®ECV<br>5. ZIAGEN | 1. ABACAVIR<br>2. EPIVIR<br>3. SUSTIVA | 1. KALETRA<br>2: ZERIT<br>5. ZIAGEN |
| Medications - Dropped | None | 1. LIPITOR<br>2. TRICOR | 1. LIPITOR<br>2. LOPID | 1. ZOCOR |
| Health Rated [1-6] | Excellent (6) | | Excellent (6) | Very Good (5) |
| Any Illness | No | | YES<br>(no description) | No<br>Food poisoning |
| Cigarettes | 1 pk/day | | No | No |

†Subject dropped out of study

TABLE 2B

Description of test subjects.

| Test Subjects<br>Variable | 005 Pretest†<br>Jun. 2, 2003 | 002 Pretest<br>May 19, 2003 | 003 Pretest<br>May 12, 2003 | 004 Pretest<br>Jun. 2, 2003 | 006 Pretest<br>Jun. 23, 2003 |
|---|---|---|---|---|---|
| Age [yrs] | 47 | 44 | 59 | 46 | 53 |
| CDC AIDS Category | C | C | C | B | C |
| Year of Diagnosis | 1998 | 1992 | 1990 | 1988 | 1989 |
| Years Infected | 6.0 | 12.0 | 14.0 | 16.0 | 15.0 |
| Exercise | | | | | |
| Times | 0 | 0 | 2.5 | 5 | 5 |
| Minutes | 0 | 0 | 30 | 60 | 120 |
| Daily activity [1-5] | Very heavy (5) | Fair (3) | Fair (3) | Very heavy (5) | Moderate (4) |
| Energy rating [0-4] | Very much (3) | Quite a lot (4) | Some (2) | Very much (3) | Quite a lot (4) |
| Medications - Current | 1. SUSTIVA<br>2. TRIZIVIR<br>3. VIREAD | 1. ANDROGEL<br>2. EPIVIR<br>3. VIRAMUNE<br>4. VIREAD<br>5. ZIAGEN | 1. ANDROGEL<br>2. EPIVIR<br>1. FORTOVASE<br>4. ZIAGEN | 1. EPIVIR<br>2. NORVIR<br>3. ZIAGEN | 1. AGENERASE<br>2. COMBIVIR<br>3. NORVIR<br>4. SUSTIVA<br>5. VIREAD |
| Medications - Dropped | 1. TRICOR | 1. LIPITOR<br>2. TRICOR | 1. LIPITOR | 1. LIPITOR<br>2. TRICOR | 1. TRICOR<br>2. JUVEN |
| Health Rated [1-6] | Excellent (6) | — | Good (4) | Good (4) | Very good (5) |
| Any Illness | No | Yes<br>Leg infection | No | Yes<br>Pneumonia previous 2 weeks | No |
| Clinic visits | No | Yes above | | No | No |
| Cigarettes | 0 | 0 | 0 | 0 | 0 |

| Test Subjects<br>Variable | 011 Pretest<br>Oct. 6, 2003 | 012 Pretest<br>Sep. 8, 2003 | 013 Pretest††<br>May 24, 2004 | 016 Pretest<br>Apr. 26, 2004 |
|---|---|---|---|---|
| Age [yrs] | 40 | 56 | 47 | 40 |
| CDC AIDS Category | A | C | A | A |
| Year of Diagnosis | 1994 | 1989 | 1985 | 1996 |
| Years Infected | 10.0 | 15.0 | 19.0 | 8.0 |
| Exercise | | | | |
| Times | 2 | 0 | 4 | 4.5 |
| Minutes | 45 | 0 | 45 | 45 |
| Daily activity [1-5] | Fair (3) | Fair (3) | Moderate (4) | Moderate (4) |
| Energy rating [0-4] | Very much (3) | Some (2) | Quite a lot (4) | Little (1) |
| Medications - Current | 1. EPIVIR<br>2. SUSTIVA<br>3. VIREAD<br>4. ZIAGEN | 1. FORTOVASE<br>2. NORVIR<br>3. VIREAD<br>4. ZERIT<br>5. ZIAGEN | 1. EPIVIR<br>2. VIRAMUNE<br>3. VIREAD<br>4. ZIAGEN | 1. EPIVIR<br>2. SUSTIVA<br>3. ZERIT |
| Medications - Dropped | 1. TRICOR | 1. TRICOR | None | 1. LIPITOR |
| Health Rated [1-6] | Very good (5) | Good (4) | Good (4) | Good (4) |
| Any Illness | No | No | No | No |
| Clinic visits | No | No | No | |
| Cigarettes | 0 | 0 | 0 | 0 |

†Subject dropped out of study;
††dropped from study due to unstable viral load and change in drug regimen during washout.

While individual estimates of exercise frequency, intensity, daily activity and energy were similar between the groups, differences in median age (placebo=39, test=47 years) and years since HIV-1 diagnosis (placebo=10.5, test=14.5) suggested an increase risk of dyslipidemia and lipoatrophy in the CLA formulation group. Further support for this increase risk the test group can be found in the description of subjects according to CDC HIV status. In the placebo group, four subjects were classified as category A status and two as category B status. The test group had two category A, one category B and four category C (increasing severity and complications) subjects.

Antiretroviral regimens for placebo and test subjects were comparable (Table 3). Two subjects in the placebo group (S010; S018) and two subjects in the test group (S012; S016) received stavudine (Zerit®) a nucleoside analog strongly associated with lipoatrophy. Regimens for S010 (placebo) and S012 (test) also included the protease inhibitory ritonavir (Novir®) with stavudine. This addition of ritonavir to stavudine regimens may further increase the risks of lipoatrophy associated with stavudine alone.

TABLE 3

Current antiretroviral therapy of subjects completing the study.

| Antiretroviral | Placebo N = 6 (%) | CLA Formulation N = 7 (%) |
|---|---|---|
| Current Nucleoside Analog | | |
| Abacavir (Ziagen ®) | 4 (67) | 6 (86) |
| Didanosinne (Videx ®) | 2 (33) | — |
| Lamivudine (Epivir ®) | 4 (67) | 5 (71) |
| Stavudine (Zerit ®) | 2 (33) | 2 (29) |
| Tenofovir (Viread ®) | 3 (50) | 5 (71) |
| Zidovudine (Retrovir ®) | — | 1 (14) |
| Current Non-nucleoside Analog | | |
| Nevirapine (Viramune ®) | | 2 (29) |
| Current Protease Inhibitor | | |
| Amprenavir (Agenerase ®) | — | 1 (14) |
| Efarivenz (Sustiva ®) | 2 (33) | 3 (42) |
| Indinavir (Crixivan ®) | 1 | — |
| Lopinavir (Kaletra ®) | 2 (33) | — |
| Ritonavir (Novir ®) | 3 (50) | 3 (42) |
| Saquinavir (Fortovase ™, Invirase ®) | 2 (33) | 2 (29) |

Bolding indicates strong associated with lipoatrophy.

Fasting serum lipid, glucose and HIV-1 variables—Daily consumption of the CLA formulation reduced LDL cholesterol from a median of 160 mg/dL at baseline to a median of 122 mg/dL by week 12 (p<0.5). The median baseline value for placebo subjects of 124 mg/dL was significantly lower (p<0.05) than test subjects and did not change during the study (Table 3). Serum triglyceride concentrations, however, rose two-fold in the placebo group over twelve weeks (p<0.05) and were not increased from baseline in the CLA formulation group. Additionally, the CLA formulation attenuated the two-fold increase observed in the triglyceride/HDL ratio in the placebo group by 26% at week 12 (p<0.05). No changes were noted for cholesterol, HDL cholesterol, cholesterol/HDL ratio or LDL/HDL ratio between treatments or over the 12 weeks of the study within treatments.

TABLE 3

Serum lipid, glucose and HIV-1 variables at baseline, six and twelve weeks.

| Index[1] | Baseline | | Six Weeks | |
|---|---|---|---|---|
| | Placebo | CLA Formulation | Placebo | CLA Formulation |
| Cholesterol [mg/dL] | 245$^a$ (148-309) | 235$^a$ (169-328) | 230$^a$ (130-252) | 243$^a$ (193-318) |
| HDL Cholesterol [mg/dL] | 39$^a$ (29-46) | 45$^a$ (32-51) | 40$^a$ (20-48) | 45$^a$ (34-52) |
| Cholesterol/HDL | 5.8$^a$ (4.4-8.1) | 5.4$^a$ (4.4-6.5) | 5.9$^a$ (4.9-7.4) | 5.8$^a$ (4.6-7.1) |
| LDL Cholesterol[2] [mg/dL] | 124$^{ab}$ (141-186) | 160$^a$ (102-219) | 134$^{ab}$ (111-156) | 129$^b$ (80-168) |
| LDL/HDL | 3.1$^a$ (2.6-4.9) | 3.6$^a$ (2.4-4.9) | 3.0$^a$ (2.3-3.7) | 3.4$^a$ (1.9-4.0) |
| Triglycerides [mg/dL] | 217$^a$ (153-718) | 281$^a$ (116-654) | 407$^a$ (135-485) | 367$^a$ (288-585) |
| Triglyceride/HDL | 5.7$^a$ (4.0-19) | 5.7$^a$ (3.0-7.7) | 10.6$^{abc}$ (3.2-20) | 9.0$^{bc}$ (7.6-12) |
| Glucose, fasting [mg/dL] | 105$^a$ (89-119) | 107$^a$ (90-118) | 100$^a$ (96-148) | 103$^a$ (79-129) |
| Insulin, fasting [µU/mL] | 13$^a$ (5.0-22) | 9.3$^a$ (5.0-19) | 16$^a$ (3.7-89) | 8.6$^a$ (4.2-72) |
| QUICKI[3] | 0.318$^a$ (0.295-0.372) | 0.334$^a$ (0.302-0.376) | 0.313$^a$ (0.243-0.392) | 0.339$^a$ (0.252-0.397) |
| HIV-1 [log copies/mL] | 1.88$^{ab}$ (1.69-2.61) | 1.69$^a$ (1.69-2.24) | 2.32$^{ac}$ (1.69-2.79) | 1.88$^{ab}$ (1.69-2.70) |
| CD4 cells [cells/mm³] | 602$^a$ (322-1250) | 685$^a$ (377-979) | 665$^a$ (402-1394) | 523$^a$ (385-910) |

| Index[1] | Twelve Weeks | |
|---|---|---|
| | Placebo | CLA Formulation |
| Cholesterol [mg/dL] | 232$^a$ (146-300) | 271$^a$ (205-306) |

TABLE 3-continued

Serum lipid, glucose and HIV-1 variables at baseline, six and twelve weeks.

| | | |
|---|---|---|
| HDL Cholesterol [mg/dL] | $38^a$ (26-45) | $46^a$ (35-59) |
| Cholesterol/HDL | $6.3^a$ (5.3-7.3) | $5.9^a$ (4.5-6.6) |
| LDL Cholesterol[2] [mg/dL] | $109^{ab}$ (75-142) | $122^b$ (95-201) |
| LDL/HDL | $3.3^a$ (2.9-3.7) | $3.1^a$ (2.1-4.3) |
| Triglycerides [mg/dL] | $447^b$ (226-571) | $340^a$ (290-554) |
| Triglyceride/HDL | $11.1^c$ (5.9-16) | $8.2^b$ (6.2-12) |
| Glucose, fasting [mg/dL] | $98^a$ (86-110) | $105^a$ (94-116) |
| Insulin, fasting [μU/mL] | $13^a$ (5.7-21) | $8.4^a$ (8.0-18) |
| QUICKI[3] | $0.322^a$ (0.298-0.369) | $0.336^a$ (0.305-0.360) |
| HIV-1 [log copies/mL] | $2.28^c$ (1.81-2.60) | $1.98^b$ (1.69-3.07) |
| CD4 cells [cells/mm$^3$] | $666^a$ (351-1101) | $562^a$ (337-821) |

[1]All values are medians of n = 6 for the placebo group and n = 7 for the CLA Formulation group unless otherwise indicated; parenthetic values are, respectively, minimum and maximum. Different superscript letters within variables indicate significant differences (p < 0.05) using the Wilcoxon signed rank test.
[2]For LDL Cholesterol and the LDL cholesterol/HDL ratio the number of subjects per period, respectively, was 3, 2 and 1 for the placebo and 6, 4, 5 for the CLA formulation.
[3]QUICKI, quantitative insulin sensitivity check index.

Figure 14:
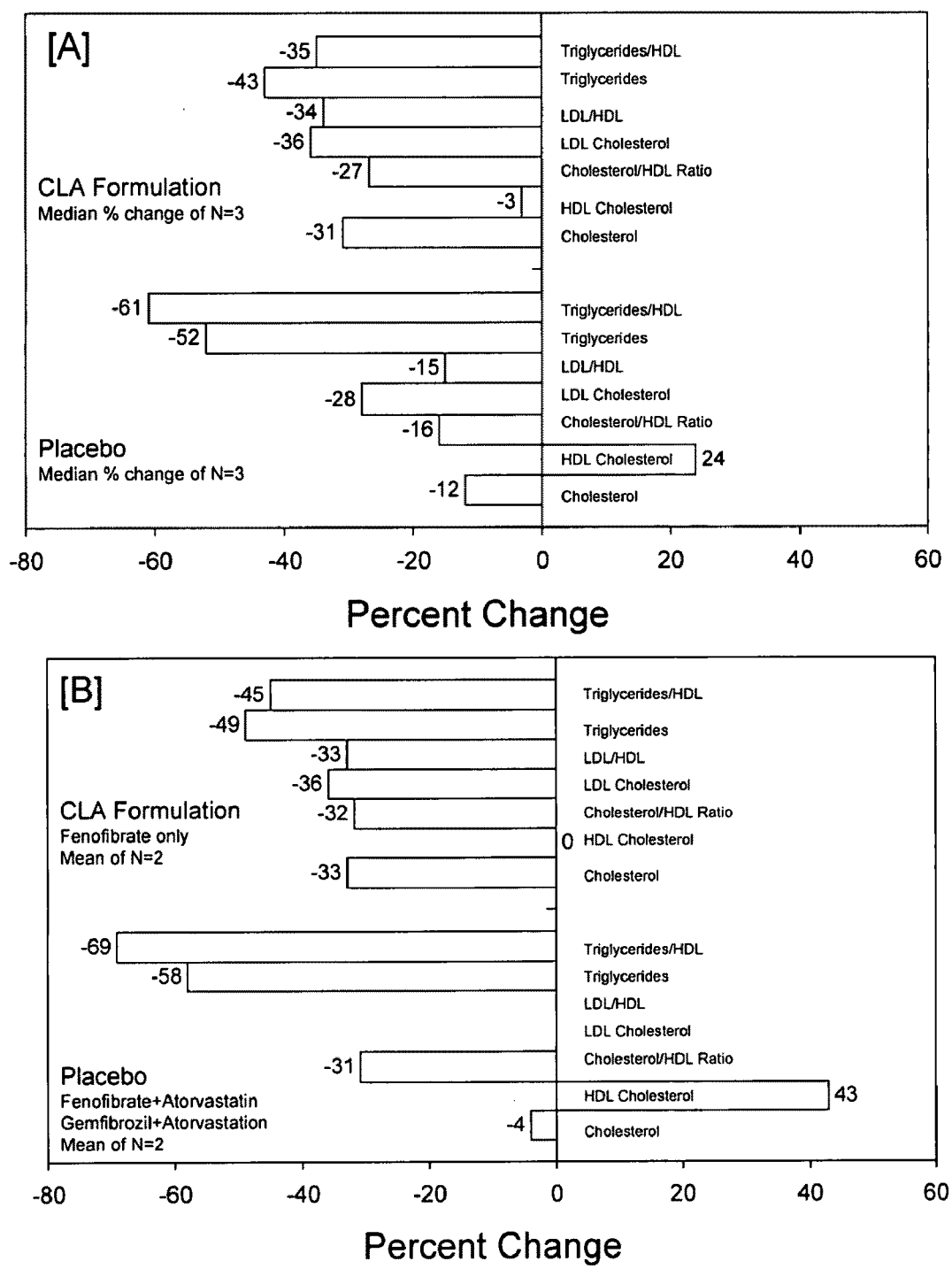
FIG. 14 depicts the percent change in serum lipid variables during weeks 12 through 15 in concert with hypolipidemic drugs. Subjects continued either the CLA formulation (three subjects) or placebo (three subjects) in addition to their cholesterol-lowering medications during weeks 12 through 15. A comparison of the median change in lipid profile for three subjects per group [A] and a comparison of the change in lipid profile of CLA subjects receiving only fenofibrate vs placebo subjects receiving fenofibrate or gemfibrozil plus atorvastatin [B].

A total of six subjects, three per treatment arm, elected to continue the study through 15 weeks while resuming their cholesterol-lowering medications. Two subjects in the CLA formulation group received only fenofibrate (S011; S012; Tricor®) and one received only atorvastatin (S016; Lipitor®). In the placebo group, two subjects received both a fibrate and a statin drug (S014; fenofibrate/atorvastatin; S017; gemfibrozil/atovastatin) and one subject received a statin only (S018; simvastatin, Zocor®). FIG. 14 clearly demonstrates that the CLA formulation did not interfere with the ability of the hypolipidemic drugs to reduce cholesterol, LDL cholesterol or triglycerides. In fact, reductions in cholesterol (−31% vs −12%) and LDL cholesterol (−36% vs −28%) were 2.6- and 1.3-fold, respectively, greater in the CLA formulation arm. While HDL levels decreased slightly in the CLA formulation arm (−3%), reduction of cholesterol/HDL (−27% vs −16%) and LDL cholesterol/HDL (−34% vs −15%) maintained the overall 2-fold superiority of the CLA formulation observed for cholesterol and LDL cholesterol. Reduction of triglycerides was similar in both groups, respectively, −43% and −49% for the CLA formulation and placebo, while reduction of triglyceride/HDL was greater in the placebo arm, −34% vs −45%.

Since the fibrate class of drugs is believed to function primarily through the peroxisome proliferator receptor alpha (PPARα) and the CLAs have been shown to bind PPARγ, it was of interest to compare the hypolipidemic effects of the subjects receiving only fenofibrate plus the CLA formulation (combined PPARα and PPARγ agonists) versus the placebo arm subjects receiving a fibrate drug (FIG. 1B). Contrasting fibrates plus the CLA formulation (n=2) versus the placebo arm subjects receiving a fibrate plus the atrovastatin (n=2) produced a surprising result. Fenofibrate in combination with the CLA formulation reduced total cholesterol 12% versus only a 4% reduction in the combination drug/placebo arm—a three-fold difference. The reduction in triglycerides was greater in the combination drug/placebo arm (−58%) than in the fibrate/CLA arm (−49%), but absolute triglyceride levels remained higher in the placebo arm than in the CLA formulation arm through 15 weeks. Because of this, LDL cholesterol values were not calculated for those two subjects in the fibrate/placebo arm. While the numbers in this subset are small, it is tempting to speculate that the combination of a fibrate and the CLA formulation represents a potentially superior regiment relative to even combinational drug therapy for the reduction of cardiovascular risk factors in this population.

No differences were observed for fasting glucose or insulin concentrations between treatments or within treatments over the twelve weeks of the study (Table 3). Further, do differences were seen in QUICKI values either between treatments or within treatments over time. However, the generally observed higher QUICKI values for the CLA formulation subjects indicating a more favorable insulin sensitivity was consistent with the lower insulin and TG/HDL ratios seen in these subjects.

At week 12, both the placebo and CLA formulation groups had experienced increases in HIV-1 viral load. This increase was attenuated in the CLA formulation group compared to placebo subjects (p<0.05, Table 3). CD4 cell counts were not affected by the CLA formulation and both the placebo and test groups exhibited no change over time.

Clinical chemistries and blood counts—There were no adverse changes in clinical chemistries or blood counts attributable to consumption of the CLA formulation.

Conclusions—This double-blinded, placebo-controlled, safety and efficacy pilot study in male, HIV-1 subjects receiving HAART has demonstrated that a formulation of conjugated linoleic acid, N-acetylcysteine and chromium is safe and well tolerated over twelve to 15 weeks. The most dramatic and consistent effects of the CLA formulation were seen with serum lipid variables. Reduction of LDL cholesterol from 160 mg/dL at baseline was 20 percent within six weeks and 24 percent at twelve weeks. Additionally, the CLA formulation prevented the increase in triglycerides and attenuated the increase in triglyceride/HDL ratio seen in the placebo group. With cholesterol-lowering medication, the CLA formulation appeared to complement efficacy, especially with the fibrate class of drugs. Attenuation of HIV-1 viral replication by the CLA formulation was also observed. Interestingly, the effects of the CLA formulation on serum lipids, complimentary hypocholesterolemic effects with fibrates, and HIV-1 replication are consistent with the role of CLA as an agonist for the PPARγ receptor. This nuclear receptor functions in both adipocytes and inflammatory cells and can mediate reduction in serum cholesterol and triglycerides as well as inflammation.

Since both insulin sensitivity and visceral adipose tissue are strongly associated with the triglyceride/HDL ratio, it is likely that the CLA formulation would demonstrate a positive effect on insulin sensitivity and body composition in an appropriately designed clinical trial.

The following examples illustrate formulations that can be utilized in the same manner as those in Example 1 with similar results. Lipoic acid is obtained from Garden State Nutritionals (West Caldwell, N.J.).

Example 7

TABLE 6

Berry-flavored dietary supplement drink mix containing chromium tricarnosinate, conjugated linoleic acid and N-acetylcysteine.

Supplement Facts
Serving Size: 1 pouch (20 g)

| Ingredient | Amount Per Serving | % Daily Value |
|---|---|---|
| Calories | 80 | |
| Total carbohydrate | 6 g | 2%* |
| Sugars | 0 g | † |
| Chromium (as chromium tricarnosinate) | 200 mcg | 166% |
| Conjugated Linoleic Acid | 6 g | † |
| N-Acetylcysteine | 1 g | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

Example 8

TABLE 7

Berry-flavored dietary supplement drink mix containing chromium carnitine, conjugated linoleic acid and lipoic acid.

Supplement Facts
Serving Size: 1 pouch (20 g)

| Ingredient | Amount Per Serving | % Daily Value |
|---|---|---|
| Calories | 78 | |
| Total carbohydrate | 6 g | 2%* |
| Sugars | 0 g | † |
| Chromium (as chromium carnitine) | 600 mcg | 166% |
| Conjugated Linoleic Acid | 6 g | † |
| Lipoic Acid | 250 mg | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

Example 9

TABLE 8

Berry-flavored dietary supplement drink mix containing chromium tricarnosinate, conjugated linoleic acid, N-acetylcysteine and lipoic acid as well as protein and a complete range of vitamins and minerals Supplement Facts
Serving Size: 3 slightly rounded scoops (57.3 g)
Servings per container: 7

| Ingredient | Amount Per Serving | % Daily Value |
|---|---|---|
| Calories | 78 | |
| Total fat | | |
| Conjugated linoleic acid (as Clarinol ™) | 3 g | 15% |
| Total carbohydrate | 11 g | 2%* |
| Sugars | 1.5 g | † |
| Dietary fiber | 2.0 g | 8% |
| Protein | 25 g | 50% |
| Vitamin A (as retinyl palmitate and 50% β-carotene) | 5,000 IU | 100% |
| Vitamin C (as sodium ascorbate) | 1,000 mg | 1,667% |
| Vitamin D (as cholecalciferol) | 200 IU | 50% |
| Vitamin E (as d-alpha-tocopheryl succinate) | 400 IU | 1,333% |
| Thiamin (as thiamin mononitrate) | 1.5 mg | 100% |
| Riboflavin | 1.7 mg | 100% |
| Niacin (as niacinamide) | 10 mg | 50% |
| Vitamin B6 (as pyridoxine HCL) | 25 mg | 1,250% |
| Folate (as folic acid) | 800 mcg | 200% |
| Vitamin B12 (as cyanocobalamin and 50% dibencozide) | 1000 mcg | 16,667% |
| Biotin | 300 mcg | 100% |
| Pantothenic acid (as D-calcium pantothenate) | 50 mg | 500% |
| Calcium (from whey protein concentrate as dicalcium phosphate) | 160 mg | 16% |
| Phosphorus (from whey protein concentrate as dicalcium phosphate) | 120 mg | 12% |
| Iodine (as potassium iodide) | 37.5 mcg | 25% |
| Magnesium (as L-carnitine magnesium citrate, magnesium oxide and from whey protein concentrate) | 240 mg | 60% |
| Zinc (as zinc arginate) | 5.25 mg | 35% |
| Selenium (as selenomethionine) | 200 mcg | 286% |
| Manganese (as manganese sulfate) | 2 mg | 100% |
| Chromium (as chromium carnosine and 50% chromium carnitine) | 400 mcg | 332% |
| Molybdenum (as sodium molybdate) | 11.25 mcg | 15% |
| N-Acetyl-L-cysteine | 2 g | — |
| L-Carnitine (as L-carnitine magnesium citrate) | 1 g | — |
| Taurine | 500 mg | — |
| Lipoic acid | 100 mg | — |
| Choline (as choline bitartrate) | 100 mg | — |
| Inositol | 100 mg | — |
| Inosine | 50 mg | — |
| Pyridoxal-alpha-ketoglutarate | 25 mg | — |
| Lutein | 6 mg | — |
| Lycopene | 3 mg | — |
| Boron (as boron citrate) | 1.5 mg | — |
| Vanadium (as vanadyl sulfate) | 50 mcg | — |

† Daily value not established.
Percent values are based on 2,000 calorie diet.
Other ingredients: Whey protein concentrate, natural and artificial flavors, calcium caseinate, sodium caseinate, glucose polymers, BeFlora Plus ™ (50% fructoligosaccharides, 47.5% soy extract, and 2.5% potato starch), guar gum, xanthan gum, silica, acesulfame potassium, and digestive enzyme blend (acid protease, amylase, amyloglucosidase, cellulare, lipase and protease.

Thus, among the various formulations taught there has been disclosed a formulation comprising a conjugated fatty acid, at least one thiol-containing compound, and at least one organic form of trivalent chromium. It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, powder, lotion, food or bar manufacturing process as well as vitamins, flavorings and carriers. Other such changes or modifications would include the use of herbs or other botanical products containing the combinations of the preferred embodiments disclosed above. Many additional modifications and variations of the embodiments described herein may be made without departing from the scope, as is apparent to those skilled in the art. The specific embodiments described herein are offered by way of example only.

What is claimed is:

1. A method for enhancing preadipocyte differentiation into adipocytes and increasing triglyceride storage in adipocytes in an animal in need thereof, said method consisting of exposing preadipocytes to a composition consisting of pharmacologically effective concentrations of conjugated linoleic acid, N-acetylcysteine and chromium carnosine.

2. The method of claim 1, wherein said conjugated linoleic acid is selected from the group consisting of a monoglyceride, a diglyceride, and a triglyceride.

3. The method of claim 1, wherein the composition further comprises a non-active ingredient selected from the group consisting of flavors, coloring agents, emulsifiers, preservatives and a pharmaceutically acceptable carrier.

4. The method of claim 1, wherein the composition is administered orally.

5. The method of claim 1, wherein enhancing preadipocyte differentiation into adipocytes and increasing triglyceride storage in adipocytes results in an increase in the number of fat-storing, subcutaneous adipocytes.

6. The method of claim 1, wherein chromium carnosine consists of inorganic, trivalent chromium plus two or three molecules of carnosine.

7. The method of claim 1 wherein enhancing preadipocyte differentiation into adipocytes and increasing triglyceride storage in adipocytes results in increased insulin sensitivity.

8. The method of claim 1 wherein enhancing preadipocyte differentiation into adipocytes and increasing triglyceride storage in adipocytes results in decreased LDL-cholesterol.

* * * * *